United States Patent
Bastiaans et al.

(10) Patent No.: US 6,555,501 B1
(45) Date of Patent: Apr. 29, 2003

(54) 4-TRIFLUOROMETHYL-3-OXAZOLYLPYRIDINES, PROCESSES FOR THEIR PREPARATION, COMPOSITIONS COMPRISING THEM AND THEIR USE AS PESTICIDES

(75) Inventors: Henricus Maria Martinus Bastiaans, Usingen (DE); Jörg Tiebes, Frankfurt (DE); Daniela Jans, Bad Homburg (DE); Waltraud Hempel, Liederbach (DE); Ulrich Sanft, Eppstein/Ts. (DE); Maria-Theresia Thönessen, Heidesheim (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/464,470

(22) Filed: Dec. 15, 1999

(30) Foreign Application Priority Data

Dec. 17, 1998 (DE) .......................... 198 58 192

(51) Int. Cl.⁷ .................. A01N 43/40; C07D 413/04
(52) U.S. Cl. .................... 504/252; 546/271.4
(58) Field of Search .................. 546/271.4; 504/252

(56) References Cited

U.S. PATENT DOCUMENTS 5,723,450 A * 3/1998 Reuschling et al. .......... 514/63

FOREIGN PATENT DOCUMENTS

WO      WO 98/57969        12/1998

OTHER PUBLICATIONS

Hoescht Schering AgrEvo GmbH application identified as AGR 98/M 213 (1998).*
Hoescht Schering AgrEvo GmbH application identified as AGR 97/M 208 (1997).*

* cited by examiner

Primary Examiner—Joseph K. McKane
Assistant Examiner—Sonya Wright
(74) Attorney, Agent, or Firm—Frommer Lawrence & Haug LLP

(57) ABSTRACT

Compounds of the formula:

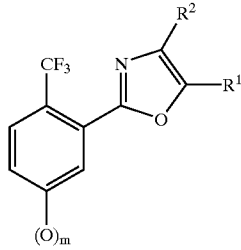

(I)

wherein $R^1$, $R^2$, and m are as defined herein, and compositions comprising them, which are suitable for controlling animal pests.

9 Claims, No Drawings

4-TRIFLUOROMETHYL-3-OXAZOLYLPYRIDINES, PROCESSES FOR THEIR PREPARATION, COMPOSITIONS COMPRISING THEM AND THEIR USE AS PESTICIDES

The invention relates to 4-trifluoromethyl-3-oxazolylpyridines, to processes for their preparation, to compositions comprising them and to their use for controlling animal pests, in particular insects, spider mites, ectoparasites and helminths.

It is already known that suitably substituted pyridines have acaricidal and insecticidal action. Thus, WO 95/07891 discloses pyridines which carry, in the 4 position, a cycloalkyl radical which is attached via a heteroatom and, in the 3 position, a group of various substituents. However, the desired action with respect to harmful organisms is not always satisfactory. Additionally, these compounds frequently have undesirable toxicological properties with respect to mammals and aquatic animals.

International Application WO-A-98/57969, which is no prior publication, proposes 4-haloalkyl-3-heterocyclylpyridines and -pyrimidines for use as pesticides.

It was an object of the present invention to provide compounds having good insecticidal and acaricidal properties, combined with low toxicity with respect to mammals and aquatic animals.

It has now been found that compounds of the formula (I), if desired also as salts, have, compared with the prior-art compounds, a broader activity spectrum with respect to animal pests, combined with more favorable toxicological properties with respect to mammals and aquatic animals.

Accordingly, the invention provides compounds of the formula (I),

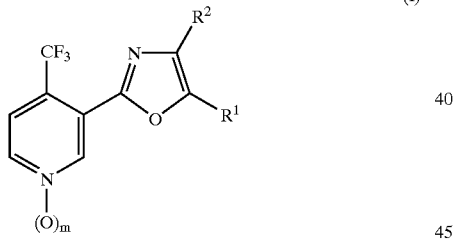

(I)

where the symbols and indices are as defined below:

m is 0 or 1;

$R^1$ and $R^2$ are a) H, $CH_3$, $-C_2H_5$, $-CH_2-CH_2-CH_3$, $-CH_2(CH_3)_2$ or cyclopropyl or b) $-CH_3$, $-CH_2XR^3$, $-CHY$, $-CO_2R^4$ or $-CONR^5R^6$, where in each case one of the radicals $R^1$, $R^2$ is of the group a and the other is of the group b;

X is O, S, SO, $SO_2$ or $NR^7$;

Y is O, $BR_2$, $-O-(CH_2)_2-O-$, $((C_1-C_4)$-alkoxy$)_2$, $((C_1-C_4)$-alkylthio$)_2$, $V-(CH_2)_2$ or $_3-V$, where V=O, S, where an H atom is optionally replaced by $(C_1-C_4)$ alkyl;

$R^3$ is $R^8$, $COR^9$, $CO_2R^{10}$, $CONR^{11}R^{12}$ or, if X is O or $NR^7$, $SO_2R^{13}$, $R^4$, $R^5$, $R^6$, $R^7$, $R^8$, $R^9$, $R^{10}$, $R^{11}$, $R^{12}$, $R^{13}$ are identical or different and are independently of one another H, $(C_1-C_{10})$-alkyl, $(C_2-C_{10})$-alkenyl, $(C_2-C_{10})$-alkynyl, $(C_3-C_8)$-cycloalkyl, $(C_4-C_8)$-cycloalkenyl, $(C_6-C_8)$-cycloalkynyl, aryl or heterocyclyl, where each of the eight last-mentioned groups is unsubstituted or mono- or polysubstituted, and where, if appropriate, in each case $R^5$ and $R^6$ and $R^{11}$ and $R^{12}$ together are $-(CH_2)_4-$, $-(CH_2)_5-$, $-(CH_2)_2-O-(CH_2)_2-$ or $-(CH_2)_2-NR^4-(CH_2)_2$;

with the proviso, that the compounds in which $R^1=CO_2C_2H_5$ and $R^2=H$, $R^1=H$ and $R^2=CH_2 NHC_6H_5$, $R^1=CH_3$ and $R^2=CO_2H$, $R^1=CH_3$ and $R^2=CO_2C_2H_5$, $R^1=CH_3$ and $R^2=CON(CH_3)_2$, $R^1=CH(CH_3)_2$ and $R^2=CO_2H$, $R^1=CH(CH_3)_2$ and $R^2=CO_2C_2H_5$ are not included.

Preferred compounds of the formula (I) are, for example, 1. compounds in which $R^1$ is H and $R^2$ is a radical of the group b;
2. compounds in which $R^1$ is a radical of the group b and $R^2$ is H,
3. compounds in which $R^1$ is a radical of the group a, with the exception of hydrogen, and $R^2$ is a radical of the group b.

m is preferably 0.

If m=1 and $R^1$ or $R^2=CH_2S(O)_nR^3$, n is preferably 2.

From the group a, H, $CH_3$ and cyclopropyl are preferred.

From the group b, $CH_2XR^3$ and $-CONR^5R^6$ are preferred.

$R^4 \cdots {}^{13}$ are preferably a) H, $(C_1-C_{10})$-alkyl, $(C_2-C_{10})$-alkenyl, $(C_2-C_{10})$-alkynyl, $(C_3-C_8)$-cycloalkyl, $(C_4-C_8)$-cycloalkenyl, $(C_6-C_8)$-cycloalkynyl, where the six last-mentioned radicals are unsubstituted or substituted by one or more radicals from the group consisting of:

halogen, cyano, citro, hydroxyl, $-C(=W)R^{14}$, $-C(=NOR^{10})R^{14}$, $-C(=NNR^{14}{}_2)R^{14}$, $-C(=W)OR^{14}$, $-C(=W)NR^{14}{}_2$, $-OC(=W)R^{14}$, $-OC(=W)OR^{14}$, $-NR^5C(=W)R^{14}$, $-N[C(=W)R^{14}]_2$, $-NR^{14}C(=W)OR^{14}$, $-C(=W)NR^{14}-NR^{14}{}_2$, $-C(=W)NR^{14}-NR^{14}[C(=W)R^{15}]$, $-NR^{14}-C(=W)NR^{14}{}_2$, $-NR^{14}-NR^{14}C(=W)R^{14}$, $-NR^{14}-N[C(=W)R^{14}]_2$, $-N[(C=W)R^{14}]-NR^{14}{}_2$, $-NR^{14}-NR^{14}[(C=W)WR^{14}]$, $-NR^{14}(C=NR^{14})R^{14}$, $-NR^{14}(C=NR^{14})-NR^{14}{}_2$, $-O-NR^{14}{}_2$, $-O-NR^{14}(C=W)R^{14}$, $-SO_2NR^{14}{}_2$, $-NR^{14}SO_2R^{14}$, $-SO_2OR^{14}$, $-OSO_2R^{14}$, $-OR^{14}$, $-NR^{14}{}_2$, $-SR^{14}$, $-SiR^{14}{}_3$, $-SeR^{14}$, $-PR^{14}{}_2$, $-P(=W)R^{14}{}_2$, $-SOR^{14}$, $-SO_2R^{14}$, $-PW_2R^{14}{}_2$, $-PW_3R^{14}{}_2$, aryl and heterocyclyl, the two last-mentioned radicals of which are unsubstituted or substituted by one or more radicals from the group consisting of $(C_1-C_6)$-alkyl, $(C_2-C_6)$-alkenyl, $(C_2-C_6)$-alkynyl, $(C_3-C_8)$-cycloalkyl, $(C_4-C_8)$-cycloalkenyl, $(C_6-C_8)$-cycloalkynyl, $(C_1-C_6)$-haloalkyl, $(C_2-C_6)$-haloalkenyl, $(C_2-C_6)$-haloalkynyl, halogen, $-OR^{14}$, $-NR^{14}{}_2$, $-SR^{14}$, $-SiR^{14}{}_3$, $-C(=W)R^{14}$, $-C(=W)OR^{14}$, $-C(=W)NR^{14}{}_2$, $-SOR^{14}$, $-SO_2R^{14}$, nitro, cyano and hydroxyl, b) aryl, which is unsubstituted or substituted by one or more radicals from the group consisting of $(C_1-C_6)$-alkyl, $(C_2-C_6)$-alkenyl, $(C_2-C_6)$-alkynyl, $(C_3-C_8)$-cycloalkyl, $(C_4-C_8)$-cycloalkenyl and $(C_6-C_8)$-cycloalkynyl, where these six abovementioned radicals are unsubstituted or substituted by one or more radicals from the group consisting of halogen, cyano, nitro, —C(=W(R$^{14}$, —C(=W)OR$^{14}$, —C(=W)NR$^{14}_2$, —OR$^{14}$, —NR$^{14}_2$, —SR$^{14}$, —SOR$^{14}$ and —SO$_2$R$^{14}$, halogen, cyano, nitro, —C(=W)R$^{14}$, —C=NOR$^{10}$)R$^{14}$, —C(=NNR$^{14}_2$)R$^{14}$, —C(=W)OR$^{14}$, —C(=W)NR$^{14}_2$, —OC((=W)R$^{14}$, —OC(=W)OR$^{14}$, —NR$^{14}$C(=W)R$^{14}$, —[C(=W)R$^{14}$]$_2$, —NR$^{14}$C(=W)OR$^{14}$, —OR$^{14}$, —NR$^{14}_2$, —SR$^{14}$, —SiR$^{14}_3$, —PR$^{14}_2$, —SOR$^{14}$, —SO$_2$R$^{14}$, —PW$_2$R$^{14}_2$ and —PW$_3$R$^{14}_2$, c) heterocyclyl which is unsubstituted or substituted by one or more radicals from the group consisting of
(C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl and (C$_6$–C$_8$)-cycloalkynyl,
where these six abovementioned radicals are unsubstituted or substituted by one or more radicals from the group consisting of
halogen, cyano, nitro, —C(=W)R$^{14}$, —C(=W)OR$^{14}$, —C(=W)NR$^{14}_2$), OR$^{14}$, —NR$^{14}_2$, —SR$^{14}$, —SOR$^{14}$ and —SO$_3$R$^{14}$,
halogen, cyano, nitro, —C(=W(R$^{14}$, —C(=NOR$^{10}$)R$^{14}$, —C(=NNR$^{14}_2$)R$^{14}$, —C(=W)OR$^{14}$, —C(=W)NR$^{14}_2$, —OC(=W)R$^{14}$, —OC(=W)OR$^{14}$, —NR$^{14}$C(=W)R$^{14}$, —[C(=W)R$^{14}$]$_2$, —NR$^{14}$C(=W)OR$^{14}$, —OR$^{14}$—NR$^{14}_2$, —SR$^{14}$, SiR$^{14}_3$, —PR$^{14}_2$, —SOR$^{14}$, —SO$_2$R$^{14}$, —PW$_2$R$^{14}$ and —PW$_3$R$^{14}_2$,
W is O or S;
R$^{14}$ is identical or different and is hydrogen, (C$_1$–C$_6$)-alkyl, (C$_2$–C$_6$)-alkenyl, (C$_2$–C$_6$)-alkynyl, (C$_3$–C$_8$)-cycloalkyl, (C$_4$–(C$_8$)-cycloalkenyl, (C$_3$–C$_8$)-cycloalkyl-(C$_1$–C$_4$)-alkyl, (C$_4$–C$_8$)-cycloalkenyl-(C$_1$–C$_4$)alkyl, (C$_3$–C$_8$)-cycloalkyl-(C$_2$–C$_4$)alkenyl, (C$_4$–C$_8$)-cycloalkenyl-(C$_1$–C$_4$)-alkenyl, (C$_1$–C$_6$)-alkyl-(C$_3$–C$_8$)-cycloalkyl, (C$_2$–C$_6$)-alkenyl-(C$_3$–C$_8$)-cycloalkyl, (C$_2$–C$_6$)-alkynyl-(C$_3$–C$_8$)-cycloalkyl, (C$_1$–C$_6$)-alkyl-(C$_4$–C$_8$)-cycloalkenyl, (C$_2$–C$_6$)-alkenyl-(C$_4$–C$_8$)cycloalkenyl, where the fourteen last-mentioned radicals are unsubstituted or substituted by one or more, preferably 1 to 3, radicals from the group consisting of
halogen, cyano, nitro, hydroxyl, thio, amino, formyl, (C$_1$–C$_6$)-alkoxy, (C$_2$–C$_6$)-alkenyloxy, (C$_2$–C$_6$)-alkynyloxy, (C$_1$–C$_6$)-haloalkyloxy, (C$_2$–C$_6$)-haloalkenyloxy, (C$_2$–C$_6$)-haloalkynyloxy, (C$_3$–C$_8$)-cycloalkoxy, (C$_4$–C$_8$)-cycloalkenyloxy, (C$_3$–C$_8$)-halocycloalkoxy, (C$_4$–C$_8$)-halocycloalkenyloxy, (C$_3$–C$_8$)-cycloalkyl-(C$_1$–C$_4$)-alkoxy, (C$_4$–C$_8$)-cycloalkenyl-(C$_1$–C$_4$)-alkoxy, (C$_3$–C$_8$)-cycloalkyl-(C$_2$–C$_4$)-alkenyloxy, (C$_4$–C$_8$)-cycloalkenyl-(C$_1$–C$_4$)-alkenyloxy, (C$_1$–C$_6$)-alkyl-(C$_3$–C$_8$)-cycloalkoxy, (C$_2$–C$_6$)-alkenyl-(C$_3$–C$_8$)-cycloalkoxy, (C$_2$–C$_6$)-alkynyl-(C$_3$–C$_8$)-cycloalkoxy, (C$_1$–C$_6$)-alkyl-(C$_4$–C$_8$)-cycloalkenyloxy, (C$_2$–C$_6$)-alkenyl-(C$_4$–C$_8$)-cycloalkenyloxy, (C$_1$–C$_4$)-alkoxy-(C$_1$–C$_6$)-alkoxy, (C$_1$–C$_4$)-alkoxy-(C$_2$–C$_6$)-alkenyloxy, carbamoyl, (C$_1$–C$_6$)-mono- or -dialkylcarbamoyl, (C$_1$–C$_6$)-mono- or dihaloalkylcarbamoyl, (C$_3$–C$_8$)-mono- or dicycloalkylcarbamoyl, (C$_1$–C$_6$)-alkoxycarbonyl, (C$_3$–C$_8$)-cycloalkoxycarbonyl, (C$_1$–C$_6$)-alkanoyloxy, (C$_3$–C$_8$)-cycloalkanoyloxy, (C$_1$C$_6$)-haloalkoxycarbonyl, (C$_1$–C$_6$)-haloalkanoyloxy, (C$_1$–C$_6$)-alkanamido, (C$_1$–C$_6$)-haloalkanamido, (C$_2$–C$_6$)-alkanamido, (C$_3$–C$_8$)-cycloalkanamido, (C$_3$–C$_8$)-cycloalkyl-(C$_1$–C$_4$)-alkanamido, (C$_1$–C$_6$)-alkylthio, (C$_2$–C$_6$)-alkenylthio, (C$_2$–C$_6$)-alkynylthio, (C$_1$–C$_6$)-haloalkylthio, (C$_2$–C$_6$)-haloalkenylthio, (C$_2$–C$_6$)-haloalkynylthio, (C$_3$–C$_8$)-cycloalkylthio, (C$_4$–C$_8$)-cycloalkenylthio, (C$_3$–C$_8$)-halocycloalkylthio, (C$_4$–C$_8$)-halocycloalkenylthio, (C$_3$–C$_8$)-cycloalkyl-(C$_1$–C$_4$)-alkylthio, (C$_4$–C$_8$)cycloalkenyl-(C$_1$–C$_4$)-alkylthio, (C$_3$–C$_8$)-cycloalkyl-(C$_2$–C$_4$)-alkenylthio, (C$_4$–C$_8$)-cycloalkenyl-(C$_1$–C$_4$)-alkenylthio, (C$_1$–C$_6$)-alkyl-(C$_3$–C$_8$)-cycloalkylthio, (C$_2$–C$_6$)-alkenyl-(C$_3$–C$_8$)-cycloalkylthio, (C$_2$–C$_6$)-alkynyl-(C$_3$–C$_8$)-cycloalkylthio, (C$_1$–C$_6$)-alkyl-(C$_4$–C$_8$)-cycloalkenylthio, (C$_2$–C$_6$)-alkenyl-(C$_4$–C$_8$)-cycloalkenylthio, (C$_1$–C$_6$)-alkylsulfinyl, (C$_2$–C$_6$)-alkenylsulfinyl, (C$_2$–C$_6$)-alkoynylsulfinyl, (C$_1$–C$_6$)-haloalkylsulfinyl, (C$_2$–C$_6$)-haloalkenylsulfinyl, (C$_2$–C$_6$)-haloalkynylsulfinyl, (C$_3$–C$_8$)-cycloalkylsulfinyl, (C$_4$–C$_8$)-cycloalkenylsulfinyl, (C$_3$–C$_8$)-halocycloalkylsulfinyl, (C$_4$–C$_8$)-halocycloalkenylsulfinyl, (C$_3$–C$_8$)-cycloalkyl-(C$_1$–C$_4$)-alkylsulfinyl, (C$_4$–C$_8$)-cycloalkenyl-(C$_1$–C$_4$)-alkylsulfinyl, (C$_3$–C$_8$)-cycloalkyl-(C$_2$–C$_4$)-alkenylsulfinyl, (C$_4$–C$_8$)-cycloalkenyl-(C$_1$–C$_4$)-alkenylsulfinyl, (C$_1$–C$_6$)-alkyl-(C$_3$–C$_8$)-cycloalkylsulfinyl, (C$_2$–C$_6$)-alkenyl-(C$_3$–C$_8$)-cycloalkylsulfinyl, (C$_2$–C$_6$)-alkynyl-(C$_3$–C$_8$)-cycloalkylsulfinyl, (C$_1$–C$_6$)-alkyl-(C$_4$–C$_8$)-cycloalkenylsulfinyl, (C$_2$–C$_6$)-alkenyl-(C$_4$–C$_8$)-cycloalkenylsulfinyl, (C$_1$–C$_6$)-alkylsulfonyl, (C$_2$–C$_6$)-alkenylsulfonyl,
(C$_2$–C$_6$)-alkynylsulfonyl, (C$_1$–C$_6$)-haloalkylsulfonyl, (C$_2$–C$_6$)-haloalkenylsulfonyl, (C$_2$–C$_6$)-haloalkynylsulfonyl, (C$_3$–C$_8$)-cycloalkylsulfonyl, (C$_4$–C$_8$)-cycloalkenylsulfonyl, (C$_3$–C$_8$)-halocycloalkylsulfonyl,
(C$_4$–C$_8$) -halocycloalkenylsulfonyl, (C$_3$–C$_8$)-cycloalkyl-(C$_1$–C$_4$)-alkylsulfonyl, (C$_4$–C$_8$)-cycloalkenyl-(C$_1$–C$_4$)-alkylsulfonyl, (C$_3$–C$_8$)-cycloalkyl-(C$_2$–C$_4$)-alkenylsulfonyl, (C$_4$–C$_8$)-cycloalkenyl-(C$_1$–C$_4$)-alkenylsulfonyl, (C$_1$–C$_6$)-alkyl-(C$_3$–C$_8$)-cycloalkylsulfonyl, (C$_2$–C$_6$)-alkenyl-(C$_3$–C$_8$)-cycloalkylsulfonyl, (C$_2$–C$_6$)-alkynyl-(C$_3$–C$_8$)-cycloalkylsulfonyl, (C$_1$–C$_6$)-alkyl-(C$_4$–C$_8$)-cycloalkenylsulfonyl, (C$_2$–C$_6$)-alkenyl-(C$_4$–C$_8$)-cycloalkenylsulfonyl, (C$_1$–C$_6$)-alkylamino, (C$_2$–C$_6$)-alkenylamino, (C$_2$–C$_6$)-alkynylamino, (C$_1$–C$_6$)-haloalkylamino, (C$_2$–C$_6$)-haloalkenylamino, (C$_2$–C$_6$)-haloalkynylamino, (C$_3$–C$_8$)-cycloalkylamino, (C$_4$–C$_8$)-cycloalkenylamino, (C$_3$–C$_8$)-halocycloalkylamino, (C$_4$–C$_8$)-halocycloalkenylamino, (C$_3$–C$_8$)-cycloalkyl-(C$_1$–C$_4$)-alkylamino, (C$_4$–C$_8$)-cycloalkenyl-(C$_1$–C$_4$)-alkylamino, (C$_3$–C$_8$)-cycloalkyl-(C$_2$–C$_4$)-alkenylamino, (C$_4$–C$_8$)-cycloalkenyl-(C$_1$–C$_4$)-alkenylamino, (C$_1$–C$_6$)-alkyl-(C$_3$–C$_8$)-cycloalkylamino, (C$_2$–C$_6$)-alkenyl-(C$_3$–C$_8$)-cycloalkylamino, (C$_2$–C$_6$)-alkynyl-(C$_3$–C$_8$)-cycloalkylamino, (C$_1$–C$_6$)-alkyl-(C$_4$–C$_8$)-cycloalkenylamino, (C$_2$–C$_6$)-alkenyl-(C$_4$–C$_8$)-cycloalkenylamino, (C$_1$–C$_6$)-trialkylsilyl, aryl, aryloxy, arylthio, arylamino, aryl-(C$_1$–C$_4$)-alkoxy, aryl-(C$_2$–C$_4$)-alkenyloxy, aryl-(C$_1$–C$_4$)-alkylthio, aryl-(C$_2$–C$_4$)-alkenylthio, aryl-(C$_1$–C$_4$)-alkylamino, aryl-(C$_2$–C$_4$)-alkenylamino, aryl-(C$_1$–C$_6$)-dialkylsilyl, diaryl-(C$_1$–C$_6$)-alkylsilyl, triarylsilyl and 5- or 6-membered heterocyclyl, where the cyclic moiety of the fourteen last-mentioned radicals is unsubstituted or substituted by one or more radicals from the group consisting of
halogen, cyano, nitro, amino, hydroxyl, thio, (C$_1$–C$_4$)-alkyl, (C$_1$–C$_4$)-haloalkyl, (C$_3$–C$_8$)- cycloalkyl, $(C_1-C_4)$-alkoxy, $(C_1-C_4)$-haloalkoxy, $(C_1-C_4)$-alkylthio, $(C_1-C_4)$-haloalkylthio, $(C_1-C_4)$-alkylamino, $(C_1C_4)$-haloalkylamino formyl and $(Cl-C_4)$-alkanoyl, aryl, 5- or 6-membered heteroaromatic, where the two last-mentioned radicals are unsubstituted or substituted by one or more radicals from the group consisting of halogen, cyano, nitro, hydroxyl, thio, amino, formyl, $(C_1-C_6)$-alkoxy, $(C_2-C_6)$-alkenyloxy, $(C_2-C_6)$-alkynyloxy, $(C_1-C_6)$-haloalkyloxy, $(C_2-C_6)$-haloalkenyloxy, $(C_2-C_6)$-haloalkynyloxy, $(C_3-C_8)$-cycloalkoxy, $(C_4-C_8)$-cycloalkenyloxy, $(C_3-C_8)$-halocycloalkoxy, $(C_4-C_8)$-halocycloalkenyloxy, carbamoyl, $(C_1-C_6)$-mono- or -dialkylcarbamoyl, $(C_1-C_6)$-alkoxycarbonyl, $(C_1-C_6)$-alkanoyloxy, $(C_1-C_6)$-mono- or -dihaloalkylcarbamoyl, $(C_1-C_6)$-haloalkoxycarbonyl, $(C_1-C_6)$-haloalkanoyloxy, $(C_1-C_6)$-alkanamido, $(C1-C_6)$-haloalkanamido, $(C_2-C_6)$-alkanamido, $(C_1-C_6)$-alkylthio, $(C_2-C_6)$-alkenylthio, $(C_2-C_6)$-alkynylthio, $(C_1-C_6)$-haloalkylthio, $(C_2-C_6)$-haloalkenylthio, $(C_2-C_6)$-haloalkynylthio, $(C_3-C_8)$-cycloalkylthio, $(C_4-C_8)$-cycloalkenylthio, $(C_3-C_8)$-halocycloalkylthio, $(C_4-C_8)$-halocycloalkenylthio, $(C_1-C_6)$-alkylsulfinyl, $(C_2-C_6)$-alkenylsulfinyl, $(C_2-C_6)$-alkynylsulfinyl, $(C_1-C_6)$-haloalkylsulfinyl, $(C_2-C_6)$-haloalkenylsulfinyl, $(C_2-C_6)$-haloalkynylsulfinyl, $(C_3-C_8)$-cycloalkylsulfinyl, $(C_4-C_8)$-cycloalkenylsulfinyl, $(C_3-C_8)$-halocycloalkylsulfinyl, $(C_4-C_8)$-halocycloalkenylsulfinyl, $(C_1-C_6)$-alkylsulfonyl, $(C_2-C_6)$-alkenylsulfonyl, $(C_2-C_6)$-alkynylsulfonyl, $(C_1-C_6)$-haloalkylsulfonyl, $(C_2-C_6)$-haloalkenylsulfonyl, $(C_2-C_6)$-haloalkynylsulfonyl, $(C_3-C_8)$-cycloalkylsulfonyl, $(C_4-C_8)$-cycloalkenylsulfonyl, $(C_3-C_8)$-halocycloalkylsulfonyl, $(C_4-C_8)$-halocycloalkenylsulfonyl, $(C_1-C_6)$-alkylamino, $(C_2-C_6)$-alkenylamino, $(C_2-C_6)$-alkynylamino, $(C_1-C_6)$-haloalkylamino, $(C_2-C_6)$-haloalkenylamino, $(C_2-C_6)$-haloalkynylamino, $(C_3-C_8)$-cycloalkylamino, $(C_4-C_8)$-cycloalkenylamino, $(C_3-C_8)$-halocycloalkylamino and $(C_4-C_8)$-halocycloalkenylamino.

$R^{4 \cdots 14}$ are particularly preferably identical or different and are H, $(C_1-C_6)$-alkyl, $(C_2-C_6)$-alkenyl, $(C_2-C_6)$-alkynyl, $(C_3-C_6)$-cycloalkyl, $(C_4-C_6)$-cycloalkenyl, aryl or heterocyclyl, where each of the seven last-mentioned groups is unsubstituted or substituted by one or more radicals from the group consisting of halogen, preferably F, $(C_1-C_4)$-alkoxy, $(C_1-C_4)$-alkylthio, NR'—CO—$(C_1-C_6)$-alkyl, where R'=H or $(C_1-C_4)$-alkyl.

Particular preference is given to the following groups of compounds of the formula (I) a–f

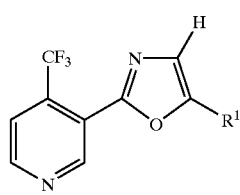
(Ia)

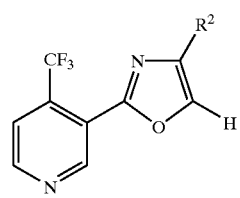
(Ib)

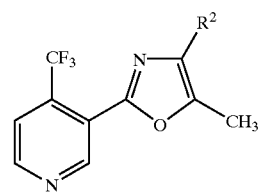
(Ic)

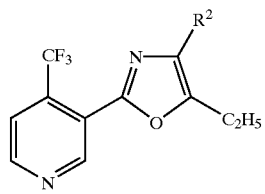
(Id)

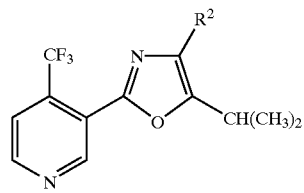
(Ie)

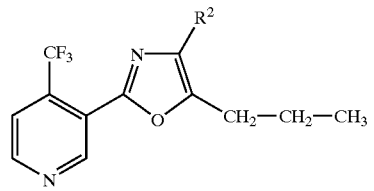
(If)

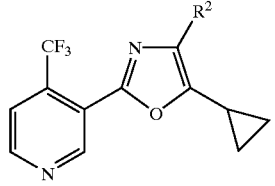
(Ig)

Very particular preference is given to compounds of the formula Ia1–Ia12

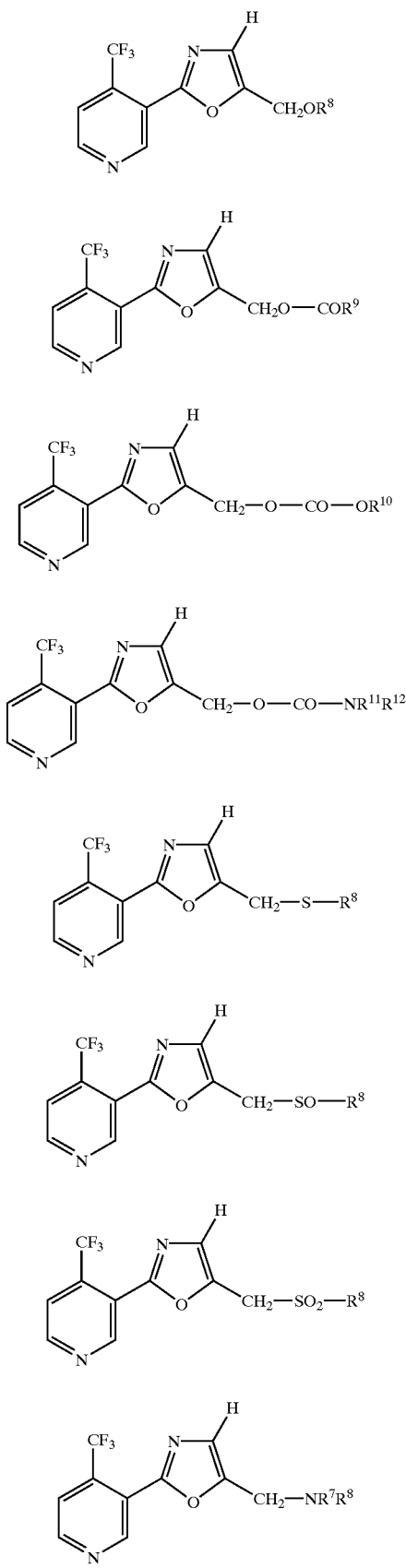
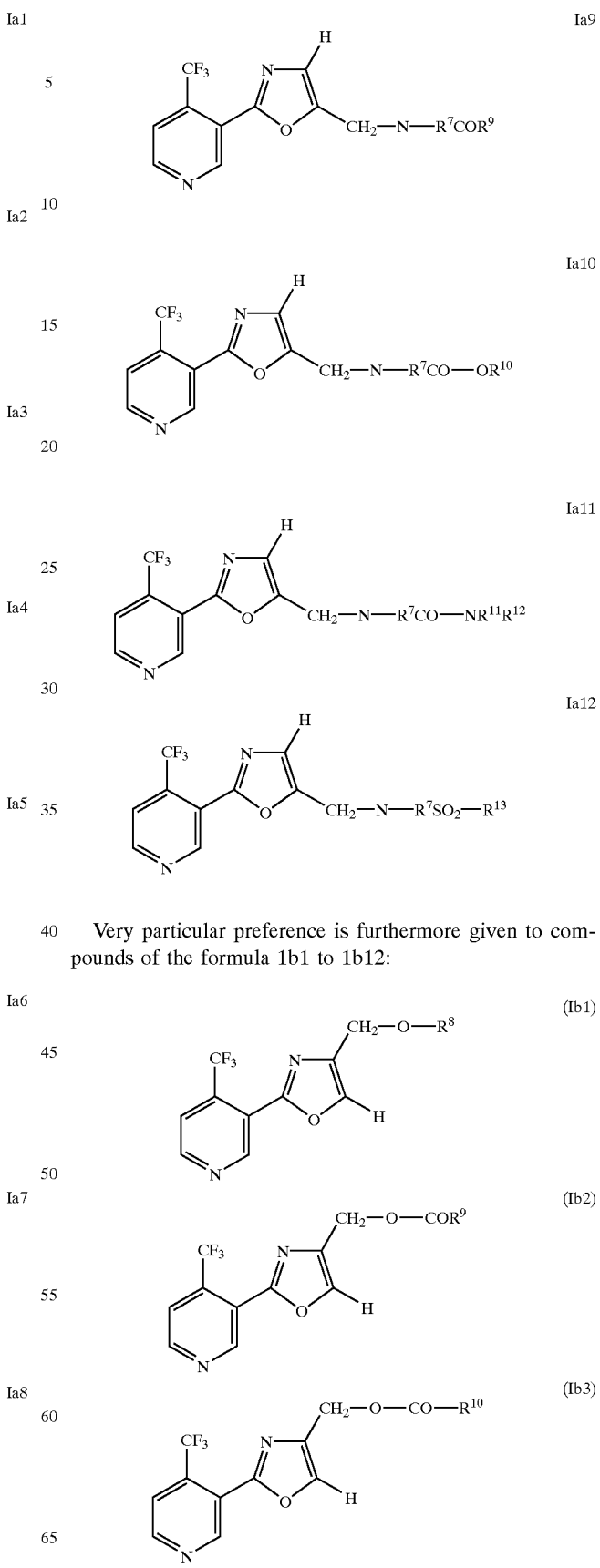
Very particular preference is furthermore given to compounds of the formula 1b1 to 1b12:

-continued (Ib4) 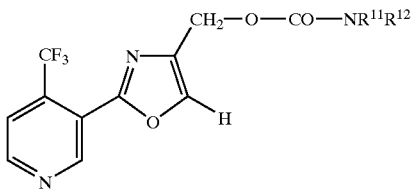

(Ib5) 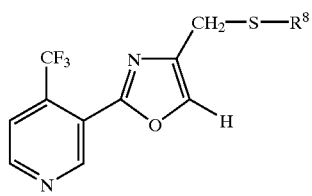

(Ib6) 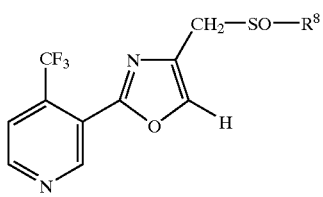

(Ib7) 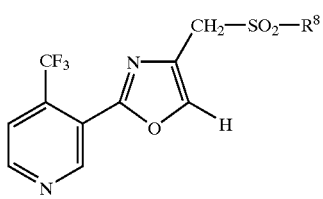

(Ib8) 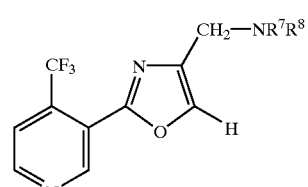

(Ib9) 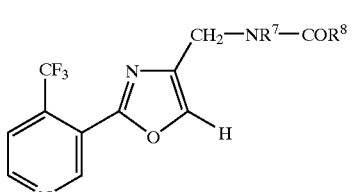

(Ib10) 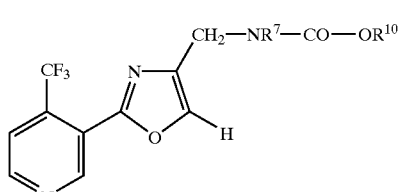

(Ib11) 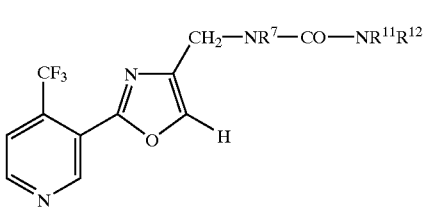

-continued (Ib12) 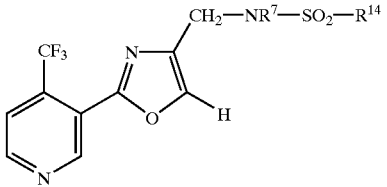

The symbols in the formulae Ia–f and 1a–12, respectively, and Ib1–12 have the abovementioned meanings and preferences.

The term "halogen" includes fluorine, chlorine, bromine and iodine.

The term "$(C_1-C_4)$-alkyl" is to be understood as a straight-chain or branched hydrocarbon radical having 1, 2, 3 or 4 carbon atoms, such as, for example, the methyl, ethyl, propyl, isopropyl, 1-butyl, 2-butyl, 2-methylpropyl or tert-butyl radical. Correspondingly, alkyl radicals having a greater range of carbon atoms are to be understood as straight-chain or branched saturated hydrocarbon radicals which contain a number of carbon atoms which corresponds to the range stated. Thus, the term "$(C_1-C_6)$-alkyl" includes the abovementioned alkyl radicals, and, for example, the pentyl, 2-methylbutyl, 1,1-dimethylpropyl, hexyl radical. The term "$(C_1-C_{10})$-alkyl" is to be understood as the abovementioned alkyl radicals, and, for example, the nonyl, 1-decyl or 2decyl radical.

"$(C_1-C_4)$-Haloalkyl" is to be understood as an alkyl group mentioned under the term "$(C_1-C_4)$-alkyl" in which one or more hydrogen atoms are replaced by the same number of identical or different halogen atoms, preferably chlorine or fluorine, such as, for example, the trifluoromethyl, the 1-fluoroethyl, the 2,2,2-trifluoroethyl, the chloromethyl, fluoromethyl, the difluoromethyl and the 1,1,2,2-tetrafluoroethyl group.

"$(C_1-C_4)$-Alkoxy" is to be understood as an alkoxy group whose hydrocarbon radical has the meaning given under the term "$(C_1-C_4)$-alkyl". The alkoxy groups embracing a greater range of carbon atoms are to be understood correspondingly.

The terms "alkenyl" and "alkynyl" having a prefix stating the range of carbon atoms denote a straight-chain or branched hydrocarbon radical having a number of carbon atoms corresponding to the range stated which comprises at least one multiple bond which may be in any position of the unsaturated radical in question. "$(C_2-C_4)$-Alkenyl" is thus, for example, the vinyl, allyl, 2-methyl-2-propenyl or 2-butenyl group; "$(C_2-C_6)$-alkenyl" denotes the abovementioned radicals and, for example, the pentenyl, 2-methylpentenyl or the hexenyl group. "$(C_2-C_4)$-Alkynyl" is, for example, the ethynyl, propargyl, 2-methyl-2-propynyl or 2-butynyl group. "$(C_2-C_6)$-Alkynyl" is to be understood as the abovementioned radicals and, for example, the 2-pentynyl or the 2-hexynyl group and "$(C_2-C_{10})$-alkynyl" is to be understood as the abovementioned radicals and, for example, the 2-octynyl or the 2-decynyl group.

"$(C_3-C_8)$-Cycloalkyl" denotes monocyclic alkyl radicals, such as the cyclopropyl, cyclobutyl, cyclopentyl, cyclohexyl, cycloheptyl or cyclooctyl radical and bicyclic alkyl radicals, such as the norbornyl radical.

The term "$(C_3-C_8)$-cycloalkyl-$(C_1-C_4)$-alkyl" is to be understood as, for example, the cyclopropylmethyl, cyclopentylmethyl, cyclohexylmethyl, cyclohexylethyl and cyclohexylbutyl radical, and the term "$(C_1-C_6)$-alkyl-$(C_3-C_8)$-cycloalkyl is to be understood as, for example, the 1-methylcyclopropyl, 1-methylcyclopentyl, 1-methylcyclohexyl, 3-hexylcyclobutyl and 4-tert-butylcyclohexyl radical.

"$(C_1-C_4)$Alkoxy-$(C_1-C_6)$-alkyloxy" is an alkoxy group as defined above which is substituted by a further alkoxy group, such as, for example, 1-ethoxyethoxy.

"$(C_3-C_8)$-Cycloalkoxy" or "$(C_3-C_8)$-cycloalkylthio" is to be understood as one of the abovementioned $(C_3-C_8)$-cycloalkyl radicals which is linked via an oxygen or sulfur atom.

"$(C_3-C_8)$Cycloalkyl-$(C_1-C_6)$-alkoxy" is, for example, the cyclopropylmethoxy, cyclobutylmethoxy, cyclopentylmethoxy, cyclohexylmethoxy, cyclohexylethoxy or the cyclohexylbutoxy group.

The term "$(C_1-C_4)$-alkyl-$(C_3-C_8)$-cycloalkoxy" is, for example, the methylcyclopropyloxy, methylcyclobutyloxy or the butylcyclohexyloxy group.

"$(C_1-C_6)$-Alkylthio" is an alkylthio group whose hydrocarbon radical has the meaning given under the term "$(C_1-C_6)$-alkyl".

Correspondingly, "$(C_1-C_6)$-alkylsulfinyl" is, for example, the methyl-, ethyl-, propyl-, isopropyl-, butyl-, isobutyl-, sec-butyl- or tert-butylsulfinyl group and "$(C_1-C_6)$-alkylsulfonyl" is, for example, the methyl-, ethyl-, propyl-, isopropyl-, butyl-, isobutyl-, sec-butyl- or tert-butylsulfonyl group.

"$(C_1-C_6)$-Alkylamino" is a nitrogen atom which is substituted by one or two identical or different alkyl radicals of the above definition.

The term "$(C_1-C_6)$-mono- or -dialkylcarbamoyl" is a carbamoyl group having one or two hydrocarbon radicals which have the meaning given under the term "$(C_1-C_6)$-alkyl)" and which, in the case of two hydrocarbon radicals, may be identical or different.

Correspondingly, "$(C_1-C_6)$-dihaloalkylcarbamoyl" is a carbamoyl group which carries two $(C_1-C_6)$-haloalkyl radicals in accordance with the above definition or one $(C_1-C_6)$-haloalkyl radical and one $(C_1-C_6)$-alkyl radical in accordance with the above definition.

"$(C_1-C_6)$-Alkanoyl" is, for example, the acetyl, propionyl, butyryl or 2-methylbutyryl group.

The term "aryl" is to be understood as an carbocyclic aromatic radical preferably having 6 to 14, in particular 6 to 12, carbon atoms, for example phenyl, naphthyl or biphenylyl, preferably phenyl.

The term "heterocyclyl" preferably denotes a cyclic radical which may be fully saturated, partially unsaturated or fully unsaturated and which may be interrupted by at least one or more identical or different atoms from the group consisting of nitrogen, sulfur or oxygen, two oxygen atoms, however, not being allowed to be directly adjacent to one another and at least one carbon atom having to be present in the ring, for example a thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine, 4H-quinolizine; piperidine, pyrrolidine, oxazoline, tetrahydrofuran, tetrahydropyran, isoxazolidine or thiazolidine radical. The term "heteroaromatic" thus embraces, from among the meanings mentioned above under "heterocyclyl", in each case the fully unsaturated aromatic heterocyclic compounds.

Heterocyclyl is particularly preferably a saturated, partially saturated or aromatic ring system having 3 to 6 ring members and 1 to 4 heteroatoms from the group consisting of O, S and N.

Heterocyclyl is very particularly preferably a radical of pyridine, pyrimidine, (1,2,4)-oxadiazole, (1,3,4)-oxadiazole, pyrrole, furan, thiophene, oxazole, thiazole, imidazole, pyrazole, isoxazole, 1,2,4-triazole, tetrazole, pyrazine, pyridazine, oxazoline, thiazoline, tetrahydrofuran, tetrahydropyran, morpholine, piperidine, piperazine, pyrroline, pyrrolidine, oxazolidine, thiazolidine, oxirane and oxetane.

"Aryl-$(C_1-C_4)$-alkoxy" is an aryl radical which is attached via a $(C_1-C_4)$-alkoxy group, for example the benzyloxy, phenylethoxy, phenylbutoxy or naphthylmethoxy radical. "Arylthio" is an aryl radical attached via a sulfur atom, for example the phenylthio or the 1- or 2-naphthylthio radical. Correspondingly, "aryloxy" is, for example, the phenoxy or 1- or 2-naphthyloxy radical.

"Aryl-$(C_1-C_4)$-alkylthio" is an aryl radical which is attached via an alkylthio radical, for example the benzylthio, naphthylmethylthio or the phenylethylthio radical.

The term "$(C_1-C_6)$-trialkylsilyl" denotes a silicon atom which carries three identical or different alkyl radicals in accordance with the above definition. Correspondingly "aryl-$(C_1-C_6)$-dialkylsilyl" is a silicon atom which carries one aryl radical and two identical or different alkyl radicals in accordance with the above definition, "diaryl-$(C_1-C_6)$-alkylsilyl" is a silicon atom which carries one alkyl radical and two identical or different aryl radicals in accordance with the above definition, and "triarylsilyl" is a silicon atom which carries three identical or different aryl radicals in accordance with the above definition.

Depending on the nature of the substituents defined above, the compounds of the formula (I) have acidic or basic properties and can form salts. If the compounds of the formula (I) carry, for example, groups such as hydroxyl, carboxyl or other groups inducing acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, further ammonia, primary, secondary and tertiary amines having $(C_1-C_4)$-alkyl radicals and also mono-, di- and trialkanolamines of $(C_1-C_4)$-alkanols. If the compounds of the formula (I) carry, for example, groups such as amino, alkylamino or other groups inducing basic properties, these compounds can be reacted with acids to give salts. Suitable acids are, for example, mineral acids, such as hydrochloric acid and sulfuric acid and phosphoric acid, organic acids, such as acetic acid and oxalic acid and acidic salts, such as $NaHSO_4$ and $KHSO_4$. The salts which can be obtained in this manner likewise have insecticidal, acaricidal and nematicidal properties.

The compounds of the formula (I) may have one or more asymmetric carbon atoms or stereoisomers on double bonds. Enantiomers or diastereomers may therefore be present. The invention embraces both the pure isomers and mixtures thereof. The mixtures of diastereomers can be separated into the isomers by customary methods, for example by selective crystallization from suitable solvents or by chromatography. Racemates can be separated into the enantiomers by customary methods. The compounds according to the invention are prepared according to methods which are known per se from the literature, as described in standard works on organic synthesis, for example Houben-Weyl, Methoden der Organischen Chemie [Methods of Organic Chemistry], Georg-Thieme-Verlag, Stuttgart.

The preparation is carried out under reaction conditions which are known and suitable for the reactions mentioned. It is also possible to employ variants which are known per se but not mentioned in more detail here.

If desired, the starting materials can also be formed in situ, such that they are not isolated from the reaction mixture but are immediately reacted further to give the compounds of the formula (I).

The present invention also relates to processes for preparing compounds of the formula (I):

Compounds of the formula (I) where $R^2$=H can be prepared, for example, by further functionalization of compound (III) or (IV):

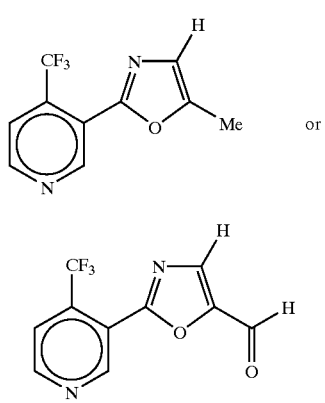

The compounds (III) and (IV) are obtained, for example, by cyclizing compounds of the formula (V):

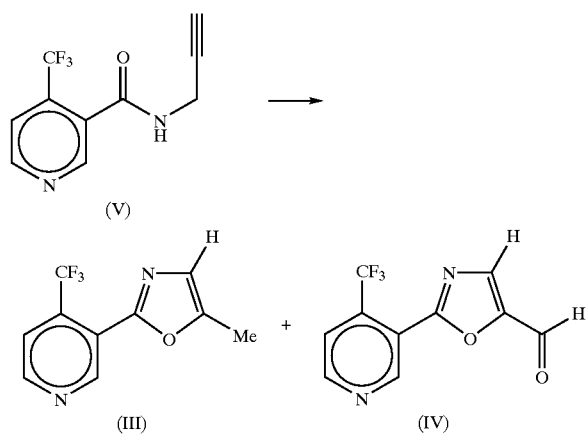

Various cyclization procedures are known from the literature, for example

KOH/ethanol/reflux (see, for example, J. Reisch et al., Pharmazie 1992, 47, 18–20)

NaH/THF/70° C. (see, for example, B. M. Nilsson et al., J. Heterocyclic Chem. 1989, 26, 269–275)

Hg (CH$_3$CO$_2$)2/glacial acetic acid/reflux (see, for example, J. Saunders et al., J. Med. Chem. 1990, 33, 1128–1130).

The starting material (V) is directly obtainable from commercially available trifluoromethylnicotinic acid and propargylamine by employing a dehydrating agent, such as dicyclohexylcarbodiimide, 1-ethyl-3-(3-dimethylaminopropyl)carbodiimide or N,N'-carbonyldiimidazole.

Compounds of the formula (I) where $R^1$=H can be obtained, for example, by further functionalization of the compound (VI)

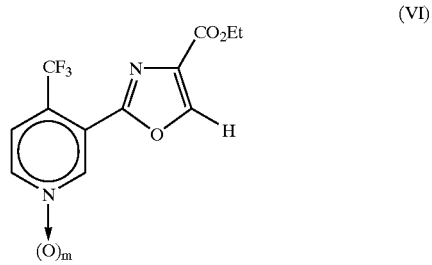

Compound (VI) can be prepared, for example, in two steps by cyclization of (VII):

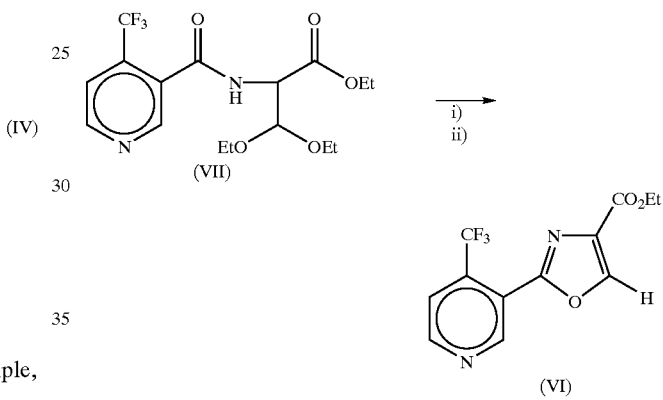

where (VII) is, for example, initially treated at 40° C. in glycol dimethyl ether with trimethylsilyl trifluoromethylsulfonate, followed by treatment with potassium tert-butoxide in tert-butanol at 0° C. to give (VI) (see, for example, S. Swaminathan et al., Tetrahedron Lett. 1998, 39, 4769–4472).

Compound (VII) can be prepared, for example, under standard conditions by acylating ethyl 2-amino-3,3,-diethoxypropionate with 4-trifluoromethyl-nicotinoyl chloride. Ethyl 2-amino-3,3-diethoxypropionate can be prepared by processes known from the literature (see, for example, S. K. Singh et al., Heterocycles 1997, 44, 379–391 or T. W. Doyle et al., Can. J. Chem. 1977, 55, 468–483).

Compounds in which $R^1$ is a radical of the group a and $R^2$ is of the group b can be prepared, for example, by further functionalization of compounds of the formula (VIII):

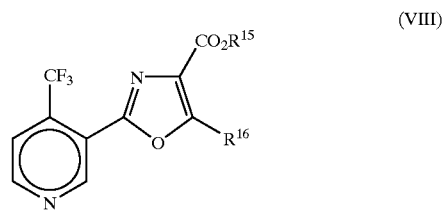

where $R^{15}$ is $CH_3$ or $C_2H_5$ and $R^{16}$ is $CH_3$, $C_2H_5$, $CH_2$—$CH_2$—$CH_3$, —$CH(CH_3)_2$ or cyclopropyl.

(VIII) can be prepared, for example, by cyclizing amides of the formula (IX).

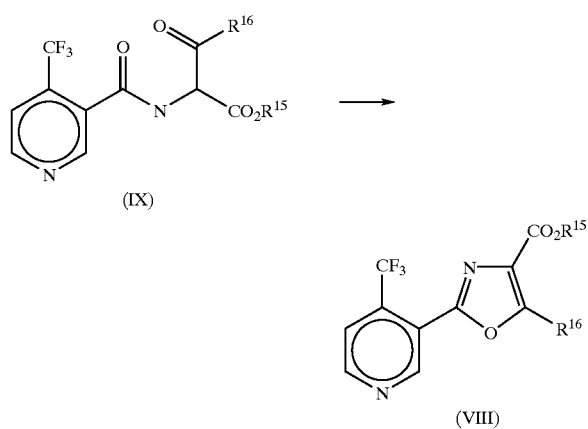

Suitable dehydrating agents which can be used for this purpose are, for example, inorganic acid chlorides, such as thionyl chloride or phosphoryl chloride, inorganic acids, such as sulfuric acid or phosphoric acid, or a mixture of acetic anhydride with an inorganic acid (see, for example, K. Meguro et al., Chem. Pharm. Buul.1986, 34, 2840–2851).

The compounds of formula (IX) can be prepared, for example, in a one-pot process from the corresponding β-ketoester (X) and 4-trifluoromethylnicotinoyl chloride.

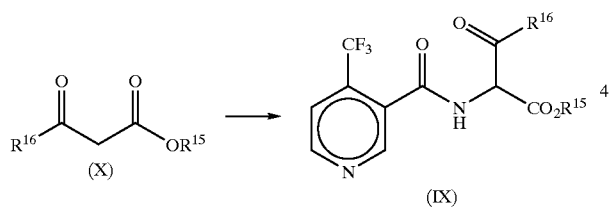

The preparation of the oxime from the β-ketoester with sodium nitrite in acetic acid, reduction with Zn/sulfuric acid and subsequent acylation is described, for example, in G. Erhart, Berichte 1949, 82, 60–63.

After the oxazole system has been constructed by condensation and cyclization reactions, the radicals $R^1$ and $R^2$ of the compounds of the formula (XL) can, if desired, be derivatized further, using the broad range of methods of organochemical synthesis familiar to the person skilled in the art.

Esters and carboxamides of the formula (I) can be obtained, for example, from compounds of the formula (XI) by methods known from the literature and familiar to the person skilled in the art, such as transesterification, aminolysis or amide formation from carboxylic acids and amines using a dehydrating agent, such as dicyclohexylcarbodiimide, 1-ethyl-3-(3-dimethylaminopropyl)carbodiimide, N,N'-carbonyldiimidazole or 2-(1H-benzotriazol-2-yl)-1,1,3,3-tetramethylammonium tetrafluoroborate.

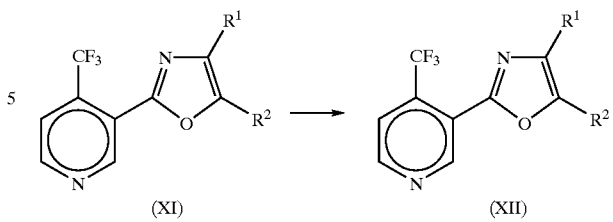

where $R^1$, $R^2$ or $R^{1'}$, $R^{2'}$ have, for example, the following meanings:

| | |
|---|---|
| $R^1$ = H; $R^2$ = $CO_2H$ | $R^{1'}$ = H; $R^{2'}$ = $CO_2R^4$, $CONR^5R^6$ |
| $R^1$ = $CO_2Et$, $CO_2H$; $R^2$ = H | $R^{1'}$ = $CO_2R^4$, $CONR^5R^6$; $R^{2'}$ = H |
| $R^1$ = $CO_2Me$, $CO_2Et$, $CO_2H$ | $R^{1'}$ = $CO_2R^4$, $CONR^5R^6$, |
| $R^2$ = Me, Et, n-Pr, i-Pr and c-Pr | $R^{2'}$ = Me, Et, i-Pr and c-Pr (c = cyclo). |

$R^4$, $R^5$ and $R^6$ are as defined above.

Compounds of formula (XI) where $R^1$=$CO_2Et$, $CO_2Me$, $CO_2H$; $R^2$=H, Me, Et, n-Pr, i-Pr and c-Pr can be obtained directly by the cyclization reactions described or by hydrolysis of the esters of cyclization products.

Compound (XI) where $R^1$=H and $R^2$=$CO_2H$ can be prepared, for example, from compound (III) or (IV) by oxidation according to processes known from the literature.

Ethers, thioethers and amines and other derivatives of the formula (XIV) can be obtained, for example, from compounds of the formula (XIII) by reactions with appropriate nucleophiles, said reactions being known from the literature and familiar to the person skilled in the art.

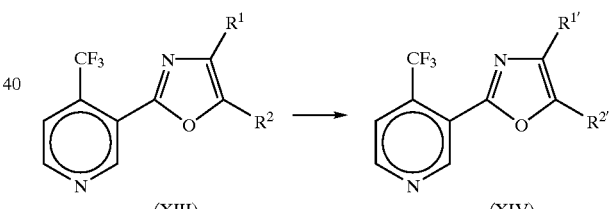

I. $R^1$ = H; $R^2$ = $CH_2Br$, $CH_2I$
II. $R^1$ = $CH_2Cl$, $CH_2I$; $R^2$ = H
III. $R^1$ = $CH_2Cl$, $CH_2I$;
R2 = M, e, Et; n-Pr, i-Pr and c-Pr;

$R^{1'}$ = H; $R^{2'}$ = $CH_2XR^3$
$R^{1'}$ = $CH_2XR^3$; $R^{2'}$ = H
$R^{1'}$ = $CH_2XR^3$,
$R^{2'}$ = Me, Et, n-Pr, i-Pr and c-Pr
X = O, S, $NR^4$ where X, $R^3$ and $R^4$ are as defined above.

Compounds of the formula (XIII) can be prepared from compounds of the formulae (III), (VI) and (VIII) by processes which are known from the literature and familiar to the person skilled in the art, for example

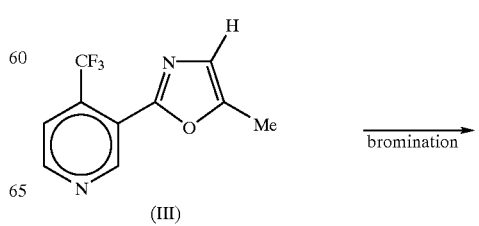

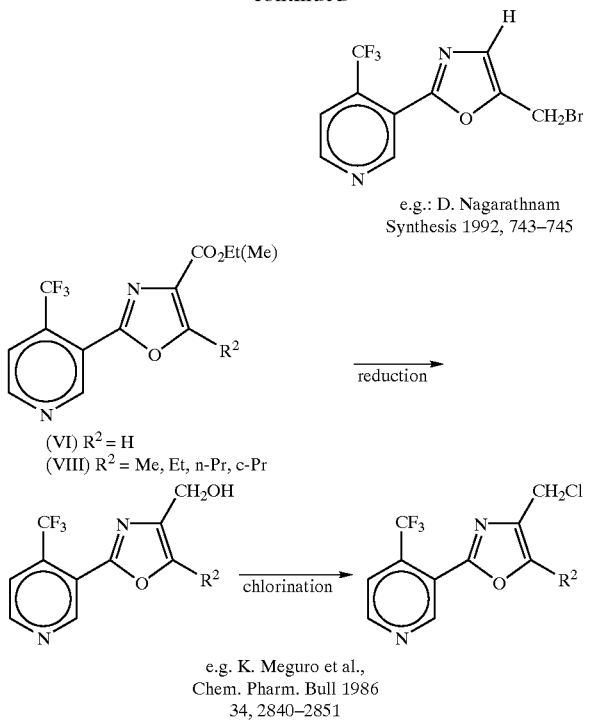

Compounds of the formula (XIV) in which $R^1$ or $R^2$ is $CH_2XR^3$ where X=S or $NR^4$, where $R^3$ or $R^4$=H or $R^3$=$R^4$=H can be reacted by methods known from the literature and familiar to the person skilled in the art to give, for example, sulfoxides, sulfones, amides and carbamates.

To synthesize compounds of the formula (I) in which m is 1, it is possible to treat compounds of the formula (I) in which m is 0 with an oxidizing agent, such as meta-chloroperbenzoic acid.

Collections of compounds of the formula (I) which can be synthesized by the abovementioned scheme may also be prepared in a parallel manner and this may be effected manually or in a semiautomated or fully automated manner. In this case, it is possible, for example, to automate the procedure of the reaction, the work-up or the purification of the products or of the intermediates. In total, this is to be understood as meaning a procedure as is described, for example, by S. H. DeWitt in "Annual Reports in Combinatorial Chemistry and Molecular Diversity: Automated synthesis", Volume 1, Verlag Escom 1997, pages 69 to 77.

A number of commercially available apparatuses as they are offered by, for example, Stem Corporation, Woodrolfe Road, Tollesbury, Essex, CM9 8SE, England or H+P Labortechnik GmbH, Bruckmannring 28, 85764 Oberschleißheim, Germany, or Firma Radleys, Shirehill, Saffron Walden, Essex, CB-11:3AZ, England may be used for the parallel procedure of the reaction and work-up. For the parallel purification of compounds of the formula (I), or of intermediates obtained during the preparation, use may be made, inter alia, of chromatography apparatuses, for example those from ISCO, Inc., 4700 Superior Street, Lincoln, Nebr. 68504, USA.

The apparatuses mentioned lead to a modular procedure in which the individual process steps are automated, but manual operations have to be performed between the process steps. This can be avoided by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula (I) may be prepared in part or fully by solid-phase-supported methods. For this purpose, individual intermediate steps or all intermediate steps of the synthesis or of a synthesis adapted to suit the procedure in question are bound to a synthetic resin.

Solid-phase-supported synthesis methods are described extensively in the specialist literature, for example Barry A. Bunin in "The Combinatorial Index", Verlag Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131–5135), in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation according to the processes described herein yields compounds of the formula (I) in the form of substance collections which are referred to as libraries. The present invention also relates to libraries which comprise at least two compounds of the formula (I).

The compounds of the formula (I) are suitable for controlling animal pests, in particular insects, arachnids, helminths and mollusks, very especially preferably for controlling insects and arachnids, which are encountered in agriculture, in livestock breeding, in forests, in the protection of stored goods and materials and in the hygiene sector, and have good plant tolerance and favorable toxicity to warm-blooded species. They are active against normally sensitive and resistant species and against all or individual development stages. The abovementioned pests include:

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Eotetranychus spp., Oligonychus spp. and Eutetranychus spp.

From the order of the Isopoda, for example, *Oniscus asselus, Armadium vulgare* and *Porcellio scaber.*

From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea madeira, Blattella germanica, Acheta domesticus,* Gryllotalpa spp., *Locusta migratoria migratorioides, Melanoplus differentialis* and *Schistocerca gregaria.*

From the order of the Isoptera, for example, Reticulitermes spp.

From the order of the Anoplura, for example, *Phylloera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonumus spp., Sitophilus spp., *Otiorrhynchus sulcatus, Cosmopolites sordidus, Ceuthorrynchus assimilis, Hypera postica,* Dermestes spp., Trogoderma, Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conodenus spp., *Melolontha melolontha, Amphirmallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopsis* and Ceratophyllus spp.

From the order of the Arachnida, for example, *Scorpio maurus* and *Latrodectus mactans.*

From the class of helminths, for example, Haemonchus, Trichostrongulus, Ostertagia, Cooperia, Chabertia, Strongyloides, Oesophagostomum, Hyostrongulus, Ancylostoma, Ascaris and Heterakis, as well as Fasciola.

From the class of the Gastropoda, for example, Deroceras spp., Arion spp., Lymnaea spp., Galba spp., Succinea spp., Biomphalaria spp., Bulinus spp. and Oncomelania spp.

From the class of Bivalva, for example, Dreissena spp.

The phytoparasitic nematodes which can be controlled according to the invention include, for example, the rootparasitic soil nematodes, such as, for example, those of the genera Meloidogyne (root gall nematodes, such as *Meloidogyne incognita, Meloidogyne hapla* and *Meloidogyne javanica*), Heterodera and Globodera (cyst-forming nematodes, such as *Globodera rostochiensis, Globodera pallida* and *Heterodera trifolii*) and of the genera Radopholus, such as *Radopholus similis,* Pratylenchus, such as *Pratylenchus neglectus, Pratylenchus penetrans* and *Pratylenchus curvitatus;*

Tylenchulus, such as *Tylenchulus semipenetrans,* Tylenchorhynchus, such as *Tylenchorhynchus dubius* and *Tylenchorhynchus claytoni,* Rotylenchus, such as *Rotylencus robustus,* Heliocotylenchus, such as *Heliocotylenchus multicinctus,* Belonoaimus, such as *Belonoaimus longicaudatus,* Longidorus, such as *Longidorus elongatus,* Trichodorus, such as *Trichodorus primitivus* and Xiphinema, such as Xiphinema index.

The nematode genera Ditylenchus (stem parasites, such as *Ditylenchus dipsaci* and *Ditylenchus destructor*), Aphelenchoides (leaf nematodes, such as *Aphelenchoides ritzemabosi*) and Anguina (blossom nematodes, such as *Anguina tritici*) can furthermore be controlled with the compounds according to the invention.

The invention also relates to compositions, in particular insecticidal and acaricidal compositions, which comprise one or more compounds of the formula (I) in addition to suitable formulation auxiliaries.

The compositions according to the invention in general comprise from 1 to 95% by weight the active compounds of the formula (I). They can be formulated in various ways, depending on how this is determined by the biological and/or chemico-physical parameters. Suitable formulation possibilities are therefore: Wettable powders (WP), emulsifiable concentrates (EC), aqueous solutions (SL), emulsions, sprayable solutions, oil- or water-based dispersions (SC), suspoemulsions (SE), dusting powders (DP), seed dressings, granules in the form of microgranules, sprayed granules, absorption granules and adsorption granules, waterdispersible granules (WG), ULV formulations, microcapsules, waxes or baits.

These individual types of formulation are known in principle and are described, for example, in: Winnacker-Küchler, "Chemische Technologie" [Chemical Technology], Volume 7, C. Hauser Vedag Munich, 4th Edition 1986; van Falkenberg, "Pesticides Formulations", Marcel Dekker N.Y., 2nd Edition 1972–73; K. Martens, "Spray Drying Handbook", 3rd Edition 1979, G. Goodwin Ltd. London.

The necessary formulation auxiliaries, i.e. carrier substances and/or surface-active substances, such as inert materials, surfactants, solvents and further additives, are likewise known and are described, for example, in: Watkins, "Handbook of Insecticide Dust Diluents and Carriers", 2nd Edition, Darland Books, Caldwell N.J.; H. v. Olphen, "Introduction to Clay Colloid Chemistry", 2nd Edition, J. Wiley & Sons, N.Y.; Marsden, "Solvents Guide", 2nd Edition, Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzfl ächenaktive Äthylenoxidaddukte" [Surface-active ethylene oxide adducts], Wiss. Verlagsgesell., Stuttgart 1967; Winnacker-Küchler, "Chemische Technologie" [Chemical Technology], Volume 7, C. Hauser Verlag Munich, 4th Edition 1986.

Combinations with other substances having a pesticidal action, fertilizers and/or growth regulators can be prepared on the basis of these formulations, for example in the form of a ready-to-use formulation or as a tank mix. Wettable powders are preparations which are uniformly dispersible in water and which, alongside the active compound, and in addition to a diluent or inert substance, also comprise wetting agents, for example polyethoxylated alkylphenols, polyethoxylated fatty alcohols or alkyl- or alkylphenolsulfonates, and dispersing agents, for example sodium ligninsulfonate or sodium 2,2'-dinaphthylmethane-6,6'-disulfonate. Emulsifiable concentrates are prepared by dissolving the active compound in an organic solvent, for example butanol, cyclohexanone, dimethylformamide, xylene or also higher-boiling aromatics or hydrocarbons, with the addition of one or more emulsifiers. Emulsifiers which can be used are, for example: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting powders are obtained, for example, by grinding the active compound with finely divided solid substances, for example talc, naturally occurring clays, such as kaolin, bentonite and pyrophillite, or diatomaceous earth. Granules can, for example, be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

In wettable powders, the active compound concentration is generally about 10 to 90% by weight, the remainder to make up 100% by weight comprising customary formulation constituents. In emulsifiable concentrates, the active compound concentration can be about 5 to 80% by weight. Dust-like formulations usually comprise 5 to 20% by weight of active compound, and sprayable solutions about 2 to 20% by weight. In granules, the content of active compound partly depends on whether the active compound is present in liquid or solid form and what granulating auxiliaries, fillers and the like are used.

In addition, the active compound formulations mentioned comprise, if appropriate, particular customary tackifiers, wetting agents, dispersing agents, emulsifiers, penetration agents, solvents, fillers or carrier substances.

For use, the concentrates in the commercially available form are diluted in the customary manner, if appropriate, for example by means of water in the case of wettable powders, emulsifiable concentrates, dispersions and in some cases also microgranules. Dust-like and granular formulations as well as sprayable solutions are usually not diluted further with additional inert substances before use.

The required amount applied varies with the external conditions, such as temperature, humidity and the like. It can vary within wide limits, for example between 0.0005 and 10.0 kg/ha or more of active compound, but is preferably between 0.001 and 5 kg/ha.

The active compounds according to the invention can be present in their commercially available formulations and in the use forms prepared from these formulations as mixtures with other active compounds, such as other pesticides, for example, insecticides or acaricides, attractants, sterilizing agents, nematicides, fungicides, growth-regulating substances or herbicides. The pesticides include, for example, phosphoric acid esters, carbamates, carboxylic acid esters, formamidines, tin compounds and substances produced by microorganisms.

Preferred partners for the mixtures are:

1. from the group of phosphorus compounds acephate, azamethiphos, azinphos-ethyl, azinphos-methyl, bromophos, bromophos-ethyl, cadusafos (F-67825), chlorethoxyphos, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, dimethoate, disulfoton, EPN, ethion, ethoprophos, etrimfos, famphur, fenamiphos, fenitriothion, fensulfothion, fenthion, fonofos, formothion, fosthiazate (ASC-66824), heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosphocarb (BAS-301), phosmet, phosphamidon, phoxim, pirimiphos, primiphosethyl, pirimiphos-methyl, profenofos, propaphos, proetamphos, prothiofos, pyraclofos, pyridapenthion, quinalphos, suiprofos, temephos, terbufos, tebupirimfos, tetrachlorvinphos, thiometon, triazophos, trichlorphon, vamidothion;

2. from the group of carbamates alanycarb (OK-135), aldicarb, 2-sec-butylphenyl methylcarbamate (BPMC), carbaryl, carbofuran, carbosulfan, cloethocarb, benfuracarb, ethiofencarb, furathiocarb, HCN-801, isoprocarb, methomyl, 5-methyl-m-cumenyl butyryl (methyl)carbamate, oxamyl, pirimicarb, propoxur, thiodicarb, thiofanox, 1-methylthio(ethylideneamino) N-methyl-N-(morpholinothio)carbamate (UC 51717), triazamate;

3. from the group of carboxylic acid esters acrinathrin, allethrin, alphametrin, 5-benzyl-3-furylmethyl (E)-(1R)-cis-2,2-di-methyl-3-(2-oxothiolan-3-ylidenemethyl)cyclopropanecarboxylate, beta-cyfluthrin, beta-cypermethrin, bioallethrin, bioallethrin ((S)-cyclopentyl isomer), bioresmethrin, bifenthrin, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyfluthrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), imiprothrin (S-41311), lambda-cyhalothrin, permethrin, pheothrin ((R) isomer), prallethrin, pyrethrins (natural products), resmethrin, tefluthrin, tetramethrin, theta-cypermethrin (TD-2344), tralomethrin, transfluthrin and zeta-cypermethrin (F-56701);

4. from the group of amidines amitraz, chlordimeform;

5. from the group of tin compounds cyhexatin, fenbutatin oxide;

6. others abamectin, ABG-9008, acetamiprid, *Anagrapha falcitera*, AKD-1022, AKD-3059, ANS-118, *Bacillus thuringiensis*, *Beauveria bassianea*, bensultap, bifenazate (D-2341), binapacryl, BJL-932, bromopropylate, BTG-504, BTG-505, buprofezin, camphechlor, cartap, chlorobenzilate, chlorfenapyr, chlorfluazuron, 2-(4-chlorophenyl)-4,5-diphenylthiophene (UBI-T 930), chlorfentezine, chromafenozide (ANS-118), CG-216, CG-217, CG-234, A-184699, 2-naphthylmethyl cyclopropanecarboxylate (Ro12-0470), cyromazin, diacloden (thiamethoxam), diafenthiuron, N-(3, 5-dichloro-4-(1,1,2,3,3,3-hexafluoro-1-propyloxy)phenyl) carbamoyl)-2-chlorobenzocarboxamide acid ethyl ester, DDT, dicofol, diflubenzuron, N-(2,3-dihydro-3-methyl-1,3-thiazol-2-ylidene)-2,4-xylidine, dinobuton, dinocap, diofenolan, DPX-062, ernamectin-benzoate (MK-244), endosulfan, ethiprole (sulfethiprole), ethofenprox, etoxazole (YI-5301), fenazaquin, fenoxycarb, fipronil, fluazuron, flumite (flufenzine, SZI-121), 2-fluoro-5-(4-(4-ethoxyphenyl)-4-methyl-1-pentyl)diphenyl ether (MTI 800), granulosis and nuclear polyhedrosis viruses, fenpyroximate, fenthiocarb, flubenzimine, flucycloxuron, flufenoxuron, flufenprox (ICI-A5683), fluproxyfen, gamma-HCH, halofenozide (RH-0345), halofenprox (MTI-732), hexaflumuron (DE__473), hexythiazox, HOI-9004, hydramethylnon (AC 217300), lufenuron, imidacloprid, indoxacarb (DPX-MP062), kanemite (AKD-2023), M-020, MTI-446, ivermectin, M-020, methoxyfenozide (Intrepid, RH-2485), milbemectin, NC-196, neemgard, nitenpyram (TI-304), 2-nitromethyl-4, 5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), pyriproxyfen (S-71639), NC-196, NC-1111, NNI-9768, novaluron (MCW-275), OK-9701, OK-9601, OK-9602, propargite, pymethrozine, pyridaben, pyrimidifen (SU-8801), RH-0345, RH-2485, RYI-210, S-1283, S-1833, SB7242, SI-8601, silafluofen, silomadine (CG-177), spinosad, SU-9118, tebufenozide, tebufenpyrad (MK-239), teflubenzuron, tetradifon, tetrasul, thiacloprid, thiocyclam, TI-435, tolfenpyrad (OMI-88), triazamate (RH-7988), triflumuron, verbutin, vertalec (Mykotal), YI-5301, The abovementioned combination partners are known active compounds, and most of them are described in Ch. R. Worthing, S. B. Walker, The Pesticide Manual, 9th Edition (1997), British Crop Protection Council.

The active compound content of the use forms prepared from the commercially available formulations can be from 0.00000001 to 95% by weight of active compound, preferably between 0.00001 and 1% by weight.

The active compounds are used in a customary manner appropriate for the use forms.

The active compounds according to the invention are also suitable for controlling endo- and ectoparasites in the veterinary medicine field and in the field of animal husbandry. The active compounds according to the invention are used here in a known manner, such as by oral use in the form of, for example, tablets, capsules, potions or granules, by means of dermal use in the form of, for example, dipping, spraying, pouring-on, spotting-on and dusting, and by parenteral use in the form of, for example, injection.

The novel compounds of the formula (I) can accordingly also particularly advantageously be used in livestock husbandry (for example cattle, sheep, pigs and poultry, such as chickens, geese and the like). In a preferred embodiment of the invention, the compounds are administered orally to the animals, if appropriate in suitable formulations and if appropriate with the drinking water or feed. Since excretion in the feces takes place in an active manner, the development of insects in the feces of the animals can be prevented very easily in this way. The dosages and formulations suitable in each case depend in particular on the species and the development stage of the stock animals and also on the level of infestation, and can easily be determined and specified by the customary methods. The novel compounds can be employed in cattle, for example, in dosages of 0.01 to 1 mg/kg of body weight.

In addition to the application methods mentioned hereinabove, the active compounds of the formula (I) according to the invention also have excellent systemic action. The active compounds can therefore also be introduced into the plants via below-ground and above-ground parts of plants (root, stem, leaf), when the active compounds are applied in liquid or solid form to the immediate surroundings of the plants (for example granules in soil application, application in flooded rice fields).

Furthermore, the active compounds according to the invention are particularly useful for treating vegetative and generatative propagation stock, such as seed of, for example, cereals, vegetables, cotton, rice, sugar beet and other crops and ornamentals, of bulbs, cuttings and tubers of other vegetatively propagated crops and ornamentals. To this end, treatment can be carried out prior to sowing or planting (for example by special seed dressing techniques, by seed dressings in liquid or solid form or by seed box treatment), during sowing or planting or after sowing or planting by special application techniques (for example seed row treatment). Depending on the application, the amount of active compound applied can vary within a relatively wide range. In general, the application rates are between 1 g and 10 kg of active compound per hectare of soil area.

The compounds of the formula (I) can also be used for controlling harmful plants in crops of known genetically modified plants or of genetically modified plants still to be developed. The transgenic plants generally have particularly advantageous properties, for example resistance to certain crop protection agents, resistance to plant diseases or pathogens of plant diseases, such as certain insects or microorganisms, such as fungi, bacteria or viruses. Other special properties relate, for example, to the harvested product, with respect to quantity, quality, shelf-life, composition and special ingredients. Thus, transgenic plants having increased starch content or a modified quality of the starch or those having a different fatty acid composition of the harvested product are known.

Preference is given to the use in economically important transgenic crops of useful and ornamental plants, for example cereals, such as wheat, barley, rye, oats, millet, rice, manioc and maize, or else crops of sugar beet, cotton, soya, rapeseed, potato, tomato, pea and other vegetable species.

The use in transgenic crops, in particular crops with resistance to insects, is, in addition to the effects with respect to harmful organisms which can be observed in other crops, frequently associated with effects which are specific for the application in the respective transgenic crop, for example a modified or specifically widened spectrum of pests which can be controlled, or modified application rates which can be used for the application.

The invention therefore also provides the use of compounds of the formula (I) for controlling harmful organisms in transgenic crop plants.

The use of the compounds according to the invention comprises, in addition to direct application to the pests, any other application where the compounds of the formula (I) act on the pests. Such indirect applications may be, for example, the use of compounds which decompose or are degraded to compounds of the formula (I), for example in the soil, the plant or the pest.

Herewith, express reference is made to the content of German Patent Application 198 58 192.0, the priority of which is claimed by the present application, and to the summary; it is incorporated into this description by reference:

The examples below serve to illustrate the invention, without implying any limitation.

A. CHEMICAL EXAMPLES

Example No. 1

5-Methyl-2-(4-tifluoromethyl-3-pyridyl)-oxazole

N-Propionyl-4-trifluoromethyinicotinamide (6.2 g) and mercury(II) acetate (0.6 g) were heated under reflux in acetic acid (250 ml) for 3 hours. The reaction mixture was subsequently concentrated and the residue was taken up in saturated sodium carbonate solution and extracted with dichloromethane. Chromatographic purification (silica gel, heptane/ethyl acetate) of the crude product gave the desired compound as a colorless oil.

$^1$H-NMR (CDCl$_3$, 300 MHz): 2.45 (s, 3H), 6.98 (s, 1H), 7.65 (d, J=5 Hz, 1H), 8.84 (d, J=5 Hz, 1H); 9.32 (s, 1H).

Pure 5-formyl-2-(4-trifluoromethyl-3-pyridyl)-oxazole as a colorless oil was obtained as a byproduct.

$^1$H-NMR (CDCl$_3$, 300 MHz): 7.77 (d, J=5 Hz, 1H), 8.05 (s, 1H), 9.00 (d, J=5 Hz, 1H), 9.43 (s, 1H), 9.94 (s, 1H).

Example No. 2

5-n-Propylthiomethyl-2-(4-trifluoromethyl-3-pyridyl)-oxazole

Sodium methoxide (130 µl, 30% in methanol) was added to a solution of 5-bromomethyl-2-(4-trifluoromethyl-3-pyridyl)-oxazole (160 mg) and n-propanethiol (60 µl), in methanol (7 ml), and the mixture was stirred at room temperature for 4 hours. Water (50 ml) was then added, and the mixture was extracted with ethyl acetate. The organic phase was washed with water, dried (MgSO$_4$), filtered and concentrated. This gave the desired product in pure form as a pale yellow oil.

$^1$H-NMR (CDCl$_3$, 300 MHz): 1.02 (t, J=7 Hz, 3H), 1.65 (quin, J=7 Hz, 2H), 2.57 (t, J=7 Hz, 2H), 3.81 (s, 2H), 7.16 (s, 1H), 7.70 (d, J=5 Hz, 1H), 8.88 (d, J=5 Hz, 1H), 9.35 (s, 1H).

The thioethers shown in the tables are prepared in a similar manner.

Example No. 3

5-Cyclopropyl-4-isopropyloxymethyl-2-(4-trifluoromethyl-3-pyridyl)-oxazole

A freshly prepared solution of sodium isopropoxide (20 mg of Na, 5 ml of 2-propanol) was added to a solution of 4-chloromethyl-5-cyclopropyl-2-(4-trifluoromethyl-3-pyridyl)-oxazole (200 mg) in 2-propanol (5 ml), and the mixture was heated under reflux for 10 hours. The reaction mixture was subsequently concentrated, mixed with water and extracted with dichloro-methane. The organic phase was washed with saturated sodium chloride solution, dried (MgSO$_4$) and filtered through silica gel. Concentration of the organic phase gave the product in pure form as a pale yellow oil.

$^1$H-NMR (CDCl$_3$, 300 MHz): 0.99–1.09 (m, 4H), 1.28 (d, J=7 Hz, 2H), 2.05–2.15 (M, 1H), 3.82 (quin, J=7 Hz, 1H), 4.56 (s, 2H), 7.73 (d, J=5 Hz, 1H), 8.80 (d, J=5 Hz, 1H), 9.39 (s, 1H).

The ethers shown in the tables are prepared in a similar manner.

Example No. 4

N-Acetyl, N-methyl-5-aminomethyl-2-(4-trifluoromethyl-3-pyridyl)-oxazole

Acetyl chloride (40 µl) was added to a solution of N-methyl-5-aminomethyl-2-(4-trifluoromethyl-3-pyridyl)-oxazole (150 mg) and triethylamine (90 µl) in dichloromethane (5 ml), and the mixture was stirred at room temperature for one hour. The mixture was then washed with water and saturated sodium bicarbonate, dried (MgSO$_4$), filtered and concentrated. This gave the pure product as a colorless oil. The $^1$H-NMR shows a mixture of rotamers (2:1 ratio).

$^1$H-NMR (CDCl$_3$; 300 MHz):

215 and 2.28 (s, 3H), 3.00 and 3.14 (s, 3H), 4.60 and 4.70 (s, 2H), 7.22 (s, 1H), 7.68 and 7.72 (d, J=5 Hz, 1 H), 8.89 and 8.93 (d, J=5H, 1 H), 9.36 (s, 1H).

The amides, carbamates, thiocarbamates, sulfonamides and urea derivatives shown in the tables are prepared in a similar manner.

Example 5

4-Ethoxycarbonyl-5-ethyl-2-(4-trifluoromethyl-3-pyridyloxazole)

A solution of sodium nitrite (4.0 g) in water (6 ml) was added to a solution of ethyl propionoylacetate (7.6 g) in acetic acid (8.0 ml) (temperature from 0 to 10° C.). After one hour at room temperature, 30% strength sulfuric acid (66 ml) and ice-water (80 ml) were added. With efficient cooling and vigorous stirring, zinc powder (62 g) was then added. After 15 minutes, the excess zinc was filtered off and the filtrate was admixed with vigorous stirring with sodium acetate (48.3 g) and freshly prepared 4-trifluoromethyl-pyridine-3-carbonyl chloride (11.5 g). After 2 hours at room temperature, the reaction mixture was extracted with dichloromethane. The organic phase was washed with saturated sodium bicarbonate solution and water, dried (MgSO$_4$), filtered and concentrated.

Chromatographic purification (silica gel, heptane/ethyl acetate) gave ethyl 2-(4-trifluoromethyl-3-amido)-acetoacetate. This compound (13.2 g), in acetic anhydride (27 ml), was admixed with sulfuric acid (2.3 mol), and the reaction mixture was subsequently stirred at 90° C. for one hour. After cooling, the reaction mixture was concentrated, rendered alkaline using saturated sodium bicarbonate solution, extracted with ethyl acetate, dried (MgSO$_4$), filtered and concentrated.

This gave the desired product in pure form as colorless crystals (m.p. 76–77° C.).

$^1$H-NMR (CDCl$_3$, 300 MHz): 1.33 (t, J=7 Hz, 3H), 1.42 (t, J=7 Hz, 3H), 3.16 (q, J=7 Hz, 2H), 4.45 (q, J=7 Hz, 2H), 7.70 (d, J=5 Hz, 1H), 8.90 (d, J=5 Hz, 1H), 9.38 (s, 1 H).

The 4-ethoxycarbonyl-5-alkyloxazole derivatives shown in the tables are prepared in a similar manner.

Example 6

5-isopropyl-4-dimethylaminocarbonyl-2-(4-trifluoromethyl-3-pyridyl)-oxazole

A suspension of 4-carboxyl-5-isopropyl-2-(4-trifluoromethyl-3-pyridyl)-oxazole (0.8 g) and 1,1'-carbonyldiimidazole (0.5 g) in 1,4-dioxane (70 ml) was stirred at 80° C. for 2 hours. At 50° C., dimethylamine was then introduced for 30 minutes, and the mixture was stirred for another hour. After cooling, water (400 ml) was added and the mixture was extracted with dichloromethane. The organic phase was washed with 5% strength aqueous potassium hydrogen sulfate and water, dried (MgSO$_4$) and filtered.

Concentration of the organic phase gave the product in pure form as colorless crystals (m.p. 91–92° C.)

¹H-NMR (CDCl₃, 300 MHz): 1.37 (d, J=7 Hz, 6H), 3.12 (s, 3H), 3.35 (s, 3H), 3.70 (quin. J=7 Hz, 1H), 7.70 (d, J=5 Hz, 1H), 8.8, (d, J=5 Hz, 1H), 9.36 (s, 1H).

The oxazole carboxamides shown in the tables are prepared in a similar manner.

TABLE 1

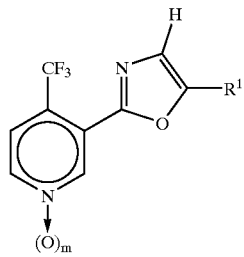

| | m | R¹ | Physical properties |
|---|---|---|---|
| 1 | 0 | CH₂SOCH₃ | |
| 2 | 0 | CON(CH₂)₄ | |
| 3 | 0 | CH₂SCH(CH₂)₅ | |
| 4 | 0 | CH₂OCH(CH₃)₂ | oil |
| 5 | 0 | CH₂OC(O)CH₂CN | |
| 6 | 0 | CONH(CH₂)₃CH₃ | |
| 7 | 0 | CONHCH₂-cyclo-C₃H₅ | |
| 8 | 0 | CON(CH₃)C₂H₅ | |
| 9 | 0 | CH₂OC(O)C₂H₅ | |
| 10 | 0 | CH₂Br | crystalline |
| 11 | 0 | CH₂OCH₂CH=CH₂ | |
| 12 | 0 | CO₂CH₂Ph | |
| 13 | 0 |  | |
| 14 | 0 | CH₂N(CH₃)COCH₃ | oil |
| 15 | 0 | CH₂OC(O)CH₂CO₂CH₃ | |
| 16 | 0 | CH₂NH₂ | |
| 17 | 0 | CH₂N(CH₃)CO₂CH₂CH=CH₂ | oil |
| 18 | 0 | CH₂N(CH₂)₅ | |
| 19 | 0 | CH₂NHCH(CH₃)₂ | |
| 20 | 0 | CH₂OCO₂CH₂CH(CH₃)₂ | |
| 21 | 0 | CH₂OC(O)CH(CH₃)₂ | |
| 22 | 0 | CH₂N(C₂H₅)COCH₃ | |
| 23 | 0 | CH₂SOCH₂-2-furyl | |
| 24 | 0 | CON(CH₃)CH₂CH=CH₂ | |
| 25 | 0 | CH₂N(CH₃)(CH₂)₂N(CH₃)₂ | |
| 26 | 0 | CHBr₂ | crystalline |
| 27 | 0 | CON(CH₃)CH₂CH₂OC(O)CH₃ | |
| 28 | 0 | CH₂OC(O)C(CH₃)₃ | |
| 29 | 0 | CH₂NH(CH₂)₂OCH₃ | |
| 30 | 0 | CH₂NHCO₂C₂H₅ | |
| 31 | 0 | CH₂NHC(O)N(CH₃)₂ | |
| 32 | 0 | CH₂SCH₂CF₃ | oil |
| 33 | 0 | CON(CH₃)CH₂-cyclo-C₃H₅ | |
| 34 | 1 | CH₂SO₂CH₃ | |
| 35 | 1 | CH₂S(O)₂CH₂CF₃ | m.p. 185–187° C. |
| 36 | 0 | CH₂N(CH₃)C(O)N(CH₃)₂ | |
| 37 | 0 | CH₂SCH₃ | oil |
| 38 | 0 | CONHC₂H₅ | |
| 39 | 0 | CON(CH₃)₂ | crystalline |
| 40 | 0 | CH₂O(CH₂)₃CH₃ | |
| 41 | 0 | CH₂NHCO-cyclo-C₃H₅ | |
| 42 | 0 | CH₂S(O)CH₂CF₃ | m.p. 111–112° C. |
| 43 | 0 | CH₂(O(CH₂)₂)₂OCH₃ | |
| 44 | 0 | CH₂OCH₂CH(CH₃)₂ | |
| 45 | 0 | CH₂OCH₂-cyclo-C₃H₅ | |
| 47 | 0 | CH₂N(C₂H₅)₂ | oil |
| 48 | 0 | CH₂NHCH₂CF₃ | |
| 49 | 0 | CH₂SC₂H₅ | |
| 50 | 0 | CH₂N(C₂H₅)CH₂CH₂OCH=CH₂ | |

TABLE 1-continued

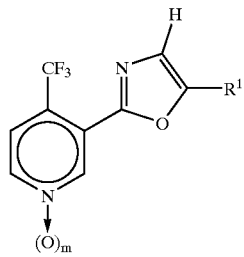

| | m | R¹ | Physical properties |
|---|---|---|---|
| 51 | 1 | CH₂SO₂(CH₂)₂OCH₃ | |
| 52 | 0 | CH₂N(CH₃)SO₂CH₃ | oil |
| 53 | 0 | CH₃ | oil |
| 54 | 0 | CH₂S(O)₂CH₂CH₂CH₃ | crystalline |
| 55 | 0 | CH(OCH(CH₃)₂)₂ | |
| 56 | 0 | CH₂NHCH₃ | oil |
| 57 | 0 |  | |
| 58 | 0 | CH₂NHCO(CH₂)₂SCH₃ | |
| 59 | 0 | CON(CH₃)CH(OCH₃)₂ | |
| 60 | 0 | CONHCH₃ | |
| 61 | 0 | CH₂N(CH₃)C(CH₃)₃ | |
| 62 | 0 | CON(CH₃)-n-C₃H₇ | |
| 63 | 0 | CH₂NHCOCH₃ | |
| 64 | 0 | CONHCH₂CH=CH₂ | |
| 65 | 0 | CONH(CH₂)₂OCH₃ | |
| 66 | 0 | CH₂NHCO-cyclo-C₄H₇ | |
| 67 | 0 | CH₂NHC₂H₅ | |
| 68 | 0 | CH₂SO₂CH₂-2-furyl | |
| 69 | 0 | CH₂SO₂(CH₂)₂OCH₃ | |
| 70 | 0 | CH₂N(CH₃)COCH₂OCH₃ | oil |
| 71 | 0 |  | |
| 72 | 0 | CH₂NHCOCH=C(H)CH₃ | |
| 73 | 0 | CH₂N(CH₃)CO₂CH₂CH(CH₃)₂ | |
| 74 | 0 | CH₂SCH₂CH=CH₂ | |
| 75 | 0 | CH₂OC(O)CH₂CH₂CH₃ | |
| 76 | 0 | CONHC₃H₇ | |
| 77 | 0 | CH₂N(CH₃)CH₂CN | |
| 78 | 0 | CH₂OCH₃ | oil |
| 79 | 0 |  | |
| 80 | 0 | CON(CH₂)₅ | |
| 81 | 0 | CH₂S(O)CH₂CH₂CH₃ | oil |
| 82 | 0 | CH₂N(CH₃)CO₂C₂H₅ | oil |
| 83 | 0 | CH₂N(CH₃)-cyclo-C₆H₁₁ | |
| 84 | 0 | CH₂N(CH₃)COC₂H₅ | oil |
| 85 | 0 | CH₂NHCOCH(CH₃)₂ | |
| 86 | 0 | CH₂SC(CH₃)₃ | |
| 87 | 0 | CH₂S(CH₂)₃OH | |
| 88 | 0 | 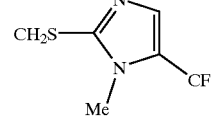 | |
| 89 | 0 | CONHCH₂C≡CH | |
| 90 | 0 | CH₂N(C₂H₅)CH₂CH=CH₂ | |
| 91 | 0 | CH₂N(C₂H₅)C(O)(CH₂)₂CH=CH₂ | |

TABLE 1-continued

Structure: pyridine with CF$_3$ and H substituents, connected to oxazole bearing R$^1$; pyridine N→(O)$_m$.

| | m | R$^1$ | Physical properties |
|---|---|---|---|
| 92 | 0 | CH$_2$N(CH$_3$)COCO$_2$CH$_3$ | oil |
| 93 | 0 | CH$_2$N(CH$_3$)SO$_2$CH$_2$CF$_3$ | oil |
| 94 | 0 | CH$_2$SCH$_2$CH(CH$_3$)$_2$ | oil |
| 95 | 0 | CH$_2$N(CH$_3$)CH$_2$CO$_2$CH$_3$ | |
| 96 | 0 | CO$_2$C(CH$_3$)$_3$ | |
| 97 | 0 | CON(CH$_3$)-n-C$_4$H$_9$ | |
| 98 | 0 | CON(CH$_3$)CH$_2$CH$_2$N(CH$_3$)$_2$ | |
| 99 | 0 | CH$_2$O(CH$_2$)$_2$CH$_3$ | |
| 100 | 0 | HC(1,3-dioxolan-2-yl) | oil |
| 101 | 0 | CH$_2$SO(CH$_2$)$_2$OCH$_3$ | |
| 102 | 0 | CON(CH$_3$)C$_2$H$_5$ | crystalline |
| 103 | 0 | CH$_2$NHCOCH$_2$CH(CH$_3$)$_2$ | |
| 104 | 0 | CH$_2$NHSO$_2$C$_2$H$_5$ | |
| 105 | 0 | | |
| 105 | 0 | CH$_2$S-(1-methylpyrrol-2-yl) | |
| 106 | 0 | CH$_2$N(CH$_3$)SO$_2$-(5-chlorothien-2-yl) | |
| 107 | 0 | CON(CH$_3$)CH$_2$CN | |
| 108 | 0 | CH$_2$Cl | |
| 110 | 0 | CH$_2$OCH$_2$CF$_3$ | |
| 111 | 0 | CH$_2$N(CH$_3$)SO$_2$C$_2$H$_5$ | oil |
| 112 | 0 | CH$_2$OC(O)N-morpholinyl | |
| 113 | 0 | CH$_2$NHCO$_2$CH$_2$CH=CH$_2$ | |
| 114 | 0 | CH$_2$N(CH$_3$)COCH$_2$-cyclo-C$_5$H$_9$ | |
| 115 | 0 | CH$_2$SCH(CH$_2$)$_4$ | |
| 116 | 0 | CH$_2$N-morpholinyl | crystalline |
| 117 | 0 | CH$_2$NHCOCH$_2$SCH$_3$ | |
| 118 | 0 | CH$_2$S(O)$_2$CH$_2$CF$_3$ | m.p. 119–120° C. |
| 119 | 0 | CH$_2$NH(CH$_2$)$_3$CH$_3$ | oil |
| 120 | 0 | CH(OC$_2$H$_5$)$_2$ | |
| 121 | 0 | CH$_2$CO$_2$C(CH$_3$)$_3$ | |
| 122 | 0 | CH$_2$CN | |
| 123 | 0 | CH$_2$SCH$_2$-2-pyrimidyl | |
| 124 | 0 | CH$_2$NHC(O)S(CH$_2$)$_2$CH$_3$ | |
| 125 | 0 | CH$_2$N(CH$_3$)CO-cyclo-C$_3$H$_5$ | oil |
| 126 | 1 | CH$_2$SO$_2$CH$_2$-2-furfuryl | |
| 127 | 0 | CH$_2$N(CH$_3$)COCH$_2$SCH$_3$ | |
| 128 | 0 | CH$_2$NHSO$_2$CH(CH$_3$)$_2$ | |
| 129 | 0 | CON(CH$_3$)(CH$_2$)$_2$CH(CH$_3$)$_2$ | |
| 130 | 0 | CH$_2$NHCO$_2$CH$_2$CH(CH$_3$)$_2$ | |
| 131 | 0 | CO$_2$-cyclo-C$_3$H$_5$ | |
| 132 | 0 | CH$_2$OCH$_2$C≡CH | |
| 133 | 0 | CH$_2$OC(O)CO$_2$CH$_3$ | |
| 134 | 0 | CH$_2$OC(O)CH$_2$CH$_2$Si(CH$_3$)$_3$ | |
| 135 | 0 | CO$_2$H | m.p. 212–214° C. |
| 136 | 0 | CH$_2$SCH$_2$CH$_3$ | oil |
| 137 | 0 | CH$_2$N(CH$_3$)CO(CH$_2$)$_2$SCH$_3$ | |
| 138 | 0 | CH$_2$CO$_2$CH$_2$Ph | |
| 139 | 0 | CO$_2$CH$_3$ | |
| 140 | 0 | CH$_2$SCH$_2$CH$_2$OH | |
| 141 | 0 | CH$_2$NHCH$_2$C≡CH | |
| 142 | 0 | CH$_2$O(CH$_2$)$_2$OCH$_3$ | |
| 143 | 0 | CH$_2$OC(O)N(CH$_3$)$_2$ | |
| 144 | 0 | CH$_2$F | |
| 145 | 0 | HC(1,3-dithian-2-yl) | |
| 146 | 0 | CH$_2$NHC(O)SCH$_3$ | |
| 147 | 0 | CH$_2$N(CH$_3$)C(O)SCH$_3$ | oil |
| 148 | 0 | CH$_2$NHCO$_2$CH$_2$CH$_2$Cl | |
| 149 | 0 | CH$_2$CO$_2$-cyclo-C$_3$H$_5$ | |
| 150 | 0 | CH$_2$NHCO(CH$_2$)$_2$CH=CH$_2$ | |
| 151 | 0 | CH$_2$N(CH$_3$)CO-cyclo-C$_4$H$_7$ | |
| 152 | 0 | CH$_2$SO$_2$CH$_3$ | |
| 153 | 0 | CH$_2$N-(1,2,3,6-tetrahydropyridin-1-yl) | |
| 154 | 0 | CH$_2$S(CH$_2$)$_2$N(CH$_3$)$_2$ | |
| 155 | 0 | CON(CH$_3$)CH$_2$CH$_2$CN | |
| 156 | 0 | CH$_2$NHC(O)SPh | |
| 157 | 0 | | |
| 157 | 0 | CH$_2$S-(1-methyltetrazol-5-yl) | |
| 158 | 0 | CONHCH$_2$CN | |
| 159 | 0 | CH(OCH$_3$)$_2$ | |
| 160 | 0 | CH$_2$SCH$_2$-2-furfuryl | |
| 161 | 0 | CH$_2$N(CH$_3$)CH(CH$_3$)$_2$ | |
| 162 | 0 | CH$_2$OCO$_2$CH$_3$ | |
| 164 | 0 | CHO | oil |
| 165 | 0 | HC(1,3-dioxan-2-yl) | |

TABLE 1-continued

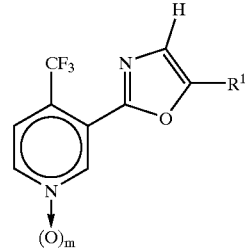

| | m | R¹ | Physical properties |
|---|---|---|---|
| 166 | 0 | [structure: dioxolane with C₂H₅] | |
| 167 | 0 | CON(CH₂)₃ | |
| 168 | 1 | CH₂S(O)₂CH₂CH₂CH₃ | m.p. 136–137° C. |
| 169 | 0 | CON[N-methylpiperazine]NCH₃ | |
| 170 | 0 | CH₂OC(O)CH₂CH(CH₃)₂ | |
| 171 | 0 | CONHCH(CH₃)₂ | |
| 172 | 0 | CH₂NHSO₂CH₂CF₃ | |
| 173 | 0 | CH₂NHCOCH₂-cyclo-C₅H₉ | |
| 174 | 0 | CH₂OH | oil |
| 175 | 0 | CON(CH₃)OCH₃ | |
| 176 | 0 | CONHC(CH₃)₃ | |
| 177 | 0 | CH₂NH-cyclo-C₃H₅ | |
| 178 | 0 | CONHCH₂CF₃ | |
| 180 | 0 | CH₂OC(O)CH=CH₂ | |
| 181 | 0 | CH₂SCH₂-cyclo-C₃H₅ | |
| 182 | 0 | CH₂SCH₂CH₂OCH₃ | |
| 183 | 0 | CH₂SCH₂-2-pyridyl | |
| 184 | 0 | CH₂NHC(O)N[morpholine]O | |
| 185 | 0 | CH₂N(CH₃)CO₂CH₂CH₂Cl | |
| 186 | 0 | CH₂OC(O)CH₃ | |
| 187 | 0 | CH₂N(CH₃)COCH(CH₃)₂ | oil |

TABLE 2

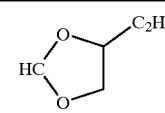

| | m | R² | Physical properties |
|---|---|---|---|
| 1 | 0 | CH₂CO₂CH₃ | |
| 2 | 0 | CH₂N(CH₃)CH(CH₃)₂ | |
| 3 | 0 | CH₂NHCOCH₂SCH₃ | |
| 4 | 0 | CH₂SCH₂CH₂OH | |
| 5 | 0 | CH₂N(C₂H₅)CH₂CH₂OCH=CH₂ | |

TABLE 2-continued

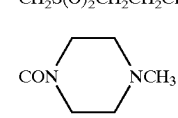

| | m | R² | Physical properties |
|---|---|---|---|
| 6 | 0 | CH₂OC(O)CH₃ | |
| 7 | 0 | CH₂OC(O)CH₂CH₂Si(CH₃)₃ | |
| 8 | 0 | CH₂S(CH₂)₃OH | |
| 9 | 1 | CH₂SO₂CH₂-2-furfuryl | |
| 10 | 0 | CH₂SO₂CH₂CF₃ | |
| 11 | 0 | CH₂OCH₂CH(CH₃)₂ | |
| 12 | 0 | CH₂S-[2-methylthio-1-methyl-5-CF₃-imidazole] | |
| 13 | 0 | CH₂N(CH₃)COcycloC₃H₅ | |
| 14 | 0 | CONH(CH₂)₂OCH₃ | m.p. 91–92° C. |
| 15 | 0 | CH₂OC₂H₅ | |
| 16 | 0 | CH₂N(C₂H₅)₂ | |
| 17 | 0 | CONH(CH₂)₃CH₃ | m.p. 69–70° C. |
| 18 | 0 | CON(CH₂)₄ | |
| 19 | 0 | CH₂SCH₂-2-furfuryl | |
| 20 | 0 | CH₂NHCO₂CH₂CH₂Cl | |
| 21 | 0 | CON(CH₃)CH₂CH₂OC(O)CH₃ | |
| 22 | 0 | CH₂CO₂CH₂Ph | |
| 23 | 0 | CH₂N-[tetrahydropyridine] | |
| 24 | 0 | CON(CH₃)CH₂CH=CH₂ | crystalline |
| 25 | 0 | CH₂NHSO₂CH(CH₃)₂ | |
| 26 | 0 | CH₂SCH₂-2-pyridyl | |
| 27 | 0 | CH₂OC(O)CH₂CO₂CH₃ | |
| 28 | 0 | CH₂Br | |
| 29 | 0 | CONHC(CH₃)₃ | |
| 30 | 0 | CH₂NHCH₃ | |
| 31 | 0 | CH₂NH(CH₂)₃CH₃ | |
| 32 | 0 | CH₂NHC(O)N(CH₃)₂ | |
| 33 | 0 | CON(CH₃)OCH₃ | |
| 34 | 0 | CH₂SCH(CH₂)₅ | |
| 35 | 0 | CH₂N(CH₃)CO₂C₂H₅ | |
| 36 | 0 | CONHCH₂-cyclo-C₃H₅ | crystalline |
| 37 | 0 | CH₂NHCO-cyclo-C₃H₅ | |
| 38 | 0 | CH₂NHCO₂CH₂CH=CH₂ | |
| 39 | 0 | CH₂OC(O)C(CH₃)₃ | |
| 40 | 0 | CH₂O(CH₂)₃CH₃ | |
| 41 | 0 | CH₂NHC(O)S(CH₂)₂CH₃ | |
| 42 | 0 | CH₂NHCO-cyclo-C₄H₇ | |
| 43 | 0 | CH₂F | |
| 44 | 0 | CH₂OCH₂C≡CH | |
| 45 | 0 | CH₂(O(CH₂)₂)₂OCH₃ | |
| 46 | 0 | CH₂O(CH₂)₂OCH₃ | |
| 47 | 0 | CH₂SO₂CH₃ | |
| 48 | 1 | CH₂SO₂CH₃ | |
| 49 | 0 | CH₂NHCH(CH₃)₂ | |
| 50 | 0 | CH₂OC(O)CH(CH₃)₂ | |
| 51 | 0 | CO₂CH₃ | m.p. 113–114° C. |
| 52 | 0 | CH₂SCH₂CH₂OCH₃ | |
| 53 | 0 | CH₂N(CH₃)SO₂CH₂CF₃ | |
| 54 | 0 | CH₂SOCH₂-2-furfuryl | |
| 55 | 0 | CH₂NHCO(CH₂)₂SCH₃ | |

TABLE 2-continued

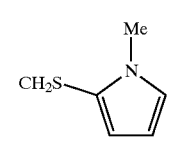

| | m | R² | Physical properties |
|---|---|---|---|
| 56 | 0 | CON(CH₃)CH(OCH₃)₂ | |
| 57 | 0 | CH₂SCH₂CH(CH₃)₂ | |
| 58 | 0 | CO₂C(CH₃)₃ | |
| 59 | 0 | CH₂N(CH₃)COCH₂SCH₃ | |
| 60 | 0 | CH₂NHC₂H₅ | |
| 61 | 1 | CH₂SO₂CH₂CF₃ | |
| 62 | 0 | CON(CH₃)(CH₂)₂CH(CH₃)₂ | |
| 63 | 0 | CH₂N(CH₃)C(CH₃)₃ | |
| 64 | 0 | CH₂N(C₂H₅)C(O)(CH₂)₂CH=CH₂ | |
| 65 | 0 | CH₂OC(O)CH₂CH₂CH₃ | |
| 66 | 0 | 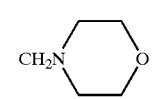 | |
| 67 | 0 | CH₂SC(CH₃)₃ | |
| 68 | 0 | CH₂N(CH₃)C(O)SCH₃ | |
| 69 | 0 |  | |
| 70 | 0 | CONHC₂H₅ | |
| 71 | 0 | CONHCH₂CN | |
| 72 | 0 | CH₂SCH₃ | oil |
| 73 | 0 | CH₂CO₂-cyclo-C₃H₅ | |
| 74 | 0 | 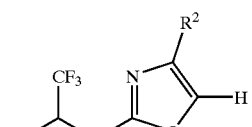 | |
| 75 | 0 | CH₂SO₂(CH₂)₂OCH₃ | |
| 76 | 0 | CO₂-cyclo-C₃H₅ | |
| 77 | 0 | CH₂NHSO₂C₂H₅ | |
| 78 | 0 | CH₂N(C₂H₅)CH₂CH=CH₂ | |
| 79 | 0 | CH₂SOCH₂CF₃ | |
| 80 | 0 | CH₂N(CH₃)-cycloC₆H₁₁ | |
| 81 | 0 | CH₂N(CH₃)CH₂CO₂CH₃ | |
| 82 | 0 | CH₂NHCH₂C≡CH | |
| 83 | 0 | CH₂S(CH₂)₂N(CH₃)₂ | |
| 84 | 0 | CONHₙ-C₃H₇ | m.p. 86–87° C. |
| 85 | 0 | CH₂SCH₂-2-pyrimidyl | |
| 86 | 0 | CH₂NHC(O)SPh | |
| 87 | 0 | CH₂N(CH₃)CO₂CH₂CH=CH₂ | |
| 88 | 0 | CH₂SOCH₃ | |
| 89 | 0 | CH₂NH-cyclo-C₃H₅ | |
| 90 | 1 | CH₂SO₂(CH₂)₂CH₃ | |
| 91 | 0 | CH₂N(CH₃)COC₂H₅ | |
| 92 | 0 | CONHCH₂CH=CH₂ | m.p. 77–78° C. |
| 93 | 0 | CH₂NH(CH₂)₂OCH₃ | |
| 94 | 0 | CH₂SCH(CH₂)₄ | |
| 95 | 0 | CH₂NHCOCH₃ | |
| 96 | 1 | CH₂SO₂(CH₂)₂OCH₃ | |
| 97 | 0 | CH₂SO(CH₂)₂CH₃ | |
| 98 | 0 | CH₂SCH₂CH=CH₂ | |
| 99 | 0 | 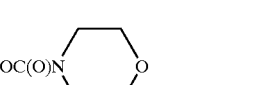 | |
| 100 | 0 | CH₂OC(O)C₂H₅ | |
| 101 | 0 | CONHCH(CH₃)₂ | oil |
| 102 | 0 | CON(CH₂)₅ | |
| 103 | 0 | CH₂N(CH₃)CO(CH₂)₂SCH₃ | |
| 104 | 0 | CH₂NHCOCH₂CH(CH₃)₂ | |
| 105 | 0 | CH₂N(CH₃)(CH₂)₂N(CH₃)₂ | |
| 106 | 0 | CH₂SO(CH₂)₂OCH₃ | |
| 107 | 0 | CON(CH₃)C₂H₅ | |
| 108 | 0 | CONHCH₂C≡CH | m.p. 161–162° C. |
| 109 | 0 | CH₂SCH₂-cyclo-C₃H₅ | |
| 110 | 0 | CH₂OCH₂CH=CH₂ | |
| 111 | 0 | CH₂N(CH₃)SO₂C₂H₅ | |
| 112 | 0 | CH₂NHC(O)SCH₃ | |
| 113 | 0 | CH₂S(CH₂)₂CH₃ | |
| 114 | 0 | CON(CH₂)₃ | |
| 115 | 0 | CH₂N(CH₃)CO-cyclo-C₄H₇ | |
| 116 | 0 | CH₂OCO₂CH₂CH(CH₃)₂ | |
| 117 | 0 | CH₂CO₂C(CH₃)₃ | |
| 118 | 0 | CON(CH₃)CH₂CH₂CN | |
| 120 | 0 | CH₂OC(O)CO₂CH₃ | |
| 121 | 0 | CON(CH₃)CH₂CN | |
| 122 | 0 | CH₂O(CH₂)₂CH₃ | |
| 123 | 0 | CH₂N(CH₃)CO₂CH₂CH₂Cl | |
| 124 | 0 | CH₂NHCH₂CF₃ | |
| 125 | 0 | CONHCH₃ | |
| 126 | 0 | CH₂OCO₂CH₃ | |
| 127 | 0 | CH₂SCH₂CF₃ | |
| 128 | 0 | CH₂NH₂ | |
| 129 | 0 | CON(CH₃)-n-C₃H₇ | |
| 130 | 0 | CH₂N(CH₃)COCH₂-cyclo-C₅H₉ | |
| 131 | 0 | 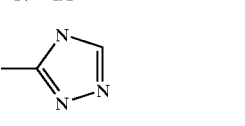 | |
| 132 | 0 | CH₂NHSO₂CH₂CF₃ | |
| 133 | 0 | CON(CH₃)-n-C₄H₉ | crystalline |
| 134 | 0 | CH₂I | |
| 135 | 0 | CH₂N(CH₃)CO₂CH₂CH(CH₃)₂ | |
| 136 | 0 | CH₂OC(O)CH₂CH(CH₃)₂ | |
| 137 | 0 | CH₂SO₂(CH₂)₂CH3 | |
| 138 | 0 |  | |
| 139 | 0 | CH₂OC(O)N(CH₃)₂ | |
| 140 | 0 | CH₂N(CH₃)COCH₃ | |
| 141 | 0 | CH₂SO₂CH₂-2-furfuryl | |
| 142 | 0 | CH₂OCH₂CF₃ | |
| 143 | 0 | CH₂NHCO₂C₂H₅ | |
| 144 | 0 | CH₂N(CH₃)C(O)N(CH₃)₂ | |
| 145 | 0 | CH₂OC(O)CH=CH₂ | |
| 146 | 0 | CON(CH₃)CH₂-cyclo-C₃H₅ | |
| 147 | 0 | CH₂N(CH₃)COCH₂OCH₃ | |

TABLE 2-continued

Structure: Pyridine with CF₃ at one position and oxazole (with R² and H substituents) attached, with (O)ₘ on pyridine N.

| | m | R² | Physical properties |
|---|---|---|---|
| 148 | 0 | $CH_2SC_2H_5$ | |
| 149 | 0 | $CH_2N(CH_2)_5$ | |
| 150 | 0 | $CO_2CH_2Ph$ | |
| 151 | 0 | $CH_2NHCOCH=CH)CH_3$ | |
| 152 | 0 | $CH_2NHCOCH_2$-cyclo-$C_5H_9$ | |
| 153 | 0 | $CH_2Cl$ | wax |
| 154 | 0 | $CH_2CN$ | |
| 155 | 0 | $CONHCH_2CF_3$ | |
| 156 | 0 | $CH_2N(C_2H_5)COCH_3$ | |
| 157 | 0 | $CH_2N(CH_3)SO_2CH_3$ | |
| 158 | 0 | $CH_2N(CH_3)CH_2CN$ | |
| 159 | 0 | $CON(CH_3)CH_2CH_2N(CH_3)_2$ | |
| 160 | 0 | $CH_2N(CH_3)COCH(CH_3)_2$ | |
| 161 | 0 | $CH_2NHCOCH(CH_3)_2$ | |
| 162 | 0 | CON-morpholine | m.p. 126–127° C. |
| 163 | 0 | $CH_2N(CH_3)_2$ | |
| 164 | 0 | $CH_2OC(O)CH_2CN$ | |
| 165 | 0 | $CH_2OCH_2$-cyclo-$C_3H_5$ | |
| 166 | 0 | $CH_2NHCO(CH_2)_2CH=CH_2$ | |
| 167 | 0 | $CH_2S$-(1-Me-tetrazol-5-yl) | |
| 168 | 0 | $CH_2NHCO_2CH_2CH(CH_3)_2$ | |
| 169 | 0 | $CO_2Et$ | oil |
| 170 | 0 | $CH_2OCH_3$ | oil |
| 171 | 0 | $CH_2S$-(4-methylthiazol-2-yl) | m.p. 65–66° C. |
| 172 | 0 | $CH_2N$-(3-CF₃-pyrazol-1-yl) | oil |
| 173 | 0 | $CONH(CH_2)_3OCH_3$ | oil |
| 174 | 0 | $CH_2OH$ | m.p. 64–65° C. |
| 175 | 0 | $CO_2H$ | m.p. 213–214° C. |
| 176 | 0 | $CH_2CH_3$ | oil |

TABLE 3a

Structure: Phenyl with CF₃ and oxazole (with R² and CH₃ substituents) attached, with (O)ₘ.

| | m | R² | Physical properties |
|---|---|---|---|
| 1 | 0 | $CH_2N(CH_3)(CH_2)_2N(CH_3)_2$ | |
| 2 | 0 | $CH_2N(CH_3)SO_2CH_3$ | |
| 3 | 0 | $CH_2SO_2(CH_2)_2OCH_3$ | |
| 4 | 0 | $CH_2N$-(tetrahydropyridyl) | |
| 5 | 0 | $CH_2NHCH_3$ | oil |
| 6 | 0 | $CH_2NHCO_2CH_2CH=CH_2$ | |
| 7 | 0 | $CH_2NHCOCH=C(H)CH_3$ | |
| 8 | 0 | $CH_2SO_2CH_2$-2-furyl | |
| 9 | 0 | $CH_2NHCH_2C≡CH$ | |
| 10 | 0 | $CH_2S$-(1-Me-pyrrol-2-yl) | |
| 11 | 0 | $CONHCH_2C≡CH$ | m.p. 105–107° C. |
| 12 | 0 | $CH_2SOCH_2CF_3$ | |
| 13 | 0 | $CH_2SC(CH_3)_3$ | |
| 14 | 0 | $CH_2OCH_2C≡CH$ | |
| 15 | 0 | $CH_2SOCH_2$-2-furyl | |
| 17 | 0 | $CH_2OCH_2$-cyclo-$C_3H_5$ | |
| 18 | 0 | $CON(CH_3)$-n-$C_3H_7$ | oil |
| 19 | 0 | $CH_2OC(O)CH_3$ | |
| 20 | 0 | $CH_2NHSO_2C_2H_5$ | |
| 21 | 0 | $CON(CH_3)$-n-$C_4H_9$ | oil |
| 22 | 0 | $CH_2N(CH_3)$-cyclo-$C_6H_{11}$ | |
| 23 | 0 | $CH_2OC(O)C_2H_5$ | |
| 24 | 0 | $CON(CH_3)CH(OCH_3)_2$ | |
| 25 | 0 | $CH_2NHC(O)S(CH_2)_2CH_3$ | |
| 26 | 0 | $CH_2SO_2CH_3$ | |
| 27 | 0 | $CH_2NHCOCH(CH_3)_2$ | |
| 28 | 0 | $CH_2N(CH_3)COCH_2SCH_3$ | |
| 29 | 0 | $CH_2CO_2$-cyclo-$C_3H_5$ | |
| 30 | 0 | $CH_2N(CH_3)CO$-cyclo-$C_4H_7$ | |
| 31 | 0 | $CH_2OC(O)N(CH_3)_2$ | |
| 32 | 0 | CON-morpholine | |
| 33 | 0 | $CH_2NH(CH_2)_3CH_3$ | |
| 34 | 0 | $CO_2C(CH_3)_3$ | |
| 35 | 0 | $CH_2SCH_2CH(CH_3)_2$ | |
| 36 | 1 | $CH_2SO_2(CH_2)_3CH_3$ | |
| 37 | 0 | $CH_2CO_2H$ | m.p. 140–141° C. |
| 38 | 0 | $CH_2NHCO(CH_2)_2CH=CH_2$ | |
| 39 | 0 | $CH_2NHC(O)N$-morpholine | |
| 40 | 0 | $CONH$-n-$C_3H_7$ | m.p. 47–49° C. |
| 41 | 0 | $CH_2N(C_2H_5)_2$ | |
| 42 | 0 | $CH_2N(CH_3)CO_2CH_2CH_2Cl$ | |

TABLE 3a-continued

[Structure: 2-(2-trifluoromethyl-phenyl)-4-R²-5-methyl-oxazole with (O)ₘ on phenyl ring]

| | m | R² | Physical properties |
|---|---|---|---|
| 43 | 0 | CONHCH$_3$ | |
| 44 | 0 | CONHCH(CH$_3$)$_2$ | |
| 45 | 0 | CONH(CH$_2$)$_2$OCH$_3$ | m.p. 62–63° C. |
| 46 | 0 | CH$_2$SCH$_2$-2-furyl | |
| 47 | 0 | CONHCH$_2$CN | |
| 48 | 0 | CH$_2$S(CH$_2$)$_2$N(CH$_3$)$_2$ | |
| 49 | 0 | CH$_2$OC(O)CH=CH$_2$ | |
| 50 | 0 | CH$_2$NHCO(CH$_2$)$_2$SCH$_3$ | |
| 51 | 0 | CH$_2$OCH$_2$CH=CH$_2$ | |
| 52 | 0 | CH$_2$CO$_2$CH$_3$ | |
| 53 | 0 | CH$_2$N(CH$_3$)COCH$_3$ | oil |
| 54 | 0 | CO$_2$CH$_3$ | |
| 55 | 0 | CH$_2$SO(CH$_2$)$_2$OCH$_3$ | |
| 56 | 0 | CON(CH$_3$)CH$_2$CH=CH$_2$ | oil |
| 57 | 1 | CH$_2$SO$_2$CH$_2$-2-furfuryl | |
| 58 | 0 | CH$_2$NH(CH$_2$)$_2$OCH$_3$ | |
| 59 | 0 | CH$_2$SCH$_2$CH=CH$_2$ | |
| 60 | 0 | CH$_2$I | |
| 61 | 0 | CH$_2$SCH$_2$-2-pyrimidyl | |
| 62 | 0 | CON(CH$_3$)CH$_2$CH$_2$N(CH$_3$)$_2$ | |
| 63 | 0 | CH$_2$N(CH$_3$)SO$_2$CH$_2$CF$_3$ | oil |
| 64 | 0 | CH$_2$O(CH$_2$)$_3$CH$_3$ | |
| 65 | 0 | CH$_2$NHCOCH$_2$-cyclo-C$_5$H$_9$ | |
| 66 | 0 | CH$_2$SO(CH$_2$)$_2$CH$_3$ | |
| 67 | 0 | CO$_2$CH$_2$Ph | |
| 68 | 0 | CH$_2$Br | |
| 69 | 0 | CH$_2$OC(O)CH(CH$_3$)$_2$ | |
| 70 | 0 | CH$_2$OC(O)CH$_2$CH(CH$_3$)$_2$ | |
| 71 | 0 | CH$_2$OCH$_2$CF$_3$ | |
| 72 | 0 | CH$_2$N(CH$_3$)CO-cyclo-C$_3$H$_5$ | |
| 73 | 0 | CH$_2$N(CH$_3$)CH$_2$CO$_2$CH$_3$ | |
| 74 | 0 | CON(CH$_3$)$_2$ | |
| 75 | 0 | CON(CH$_2$)$_4$ | |
| 76 | 0 | CH$_2$O(CH$_2$)$_2$OCH$_3$ | |
| 77 | 0 | CH$_2$NHC(O)SPh | |
| 78 | 0 | CH$_2$NHCO$_2$C$_2$H$_5$ | |
| 79 | 0 | CH$_2$S-(1,2,4-triazol-3-yl) | |
| 80 | 0 | CH$_2$N(CH$_3$)SO$_2$C$_2$H$_5$ | |
| 81 | 0 | CH$_2$NHSO$_2$CH(CH$_3$)$_2$ | |
| 82 | 0 | CH$_2$OC(O)CH$_2$CH$_2$Si(CH$_3$)$_3$ | |
| 83 | 0 | CO$_2$-cyclo-C$_3$H$_5$ | |
| 84 | 0 | CH$_2$OCH(CH$_2$)$_3$ | oil |
| 85 | 0 | CH$_2$SOCH$_3$ | |
| 86 | 0 | CON(4-methylpiperazin-1-yl) | |
| 87 | 0 | CH$_2$S(CH$_2$)$_2$CH$_3$ | |
| 88 | 0 | CH$_2$SCH$_2$-2-pyridyl | |
| 89 | 0 | CH$_2$OC(O)CH$_2$CN | |
| 90 | 0 | CH$_2$S-(1-methyl-tetrazol-5-yl) | |
| 91 | 0 | CH$_2$N(CH$_3$)COCH$_3$ | oil |
| 92 | 0 | CH$_2$CN | |
| 93 | 0 | CH$_2$OC(O)CO$_2$CH$_3$ | |
| 94 | 1 | CH$_2$SO$_2$CH$_3$ | |
| 95 | 0 | CH$_2$CON(CH$_3$)$_2$ | m.p. 85–86° C. |
| 96 | 0 | CH$_2$CO$_2$CH$_2$Ph | |
| 97 | 0 | CH$_2$SO$_2$(CH$_2$)$_2$CH3 | |
| 98 | 0 | CH$_2$N(CH$_3$)C(O)N(CH$_3$)$_2$ | |
| 99 | 0 | CONHCH$_2$-cyclo-C$_3$H$_5$ | m.p. 79–81° C. |
| 100 | 0 | CH$_2$OCH$_2$CH(CH$_3$)$_2$ | |
| 101 | 0 | CH$_2$SCH(CH$_2$)$_4$ | |
| 102 | 0 | CON(CH$_3$)OCH$_3$ | |
| 103 | 0 | CH$_2$N(CH$_3$)COCH(CH$_3$)$_2$ | |
| 104 | 0 | CH$_2$N(CH$_3$)CO$_2$CH$_2$CH(CH$_3$)$_2$ | |
| 105 | 0 | CH$_2$N(C$_2$H$_5$)COCH$_3$ | |
| 107 | 0 | CH$_2$NHCH$_2$CF$_3$ | |
| 108 | 0 | CH$_2$N(CH$_3$)COCH$_2$-cyclo-C$_5$H$_9$ | |
| 109 | 0 | CH$_2$N(CH$_3$)C(O)SCH$_3$ | |
| 110 | 0 | CONH(CH$_2$)$_3$CH$_3$ | wax |
| 111 | 0 | CH$_2$NHCO$_2$CH$_2$CH$_2$Cl | |
| 112 | 0 | CH$_2$OCO$_2$CH$_3$ | |
| 113 | 0 | CH$_2$NH$_2$ | |
| 114 | 0 | CON(CH$_3$)C$_2$H$_5$ | |
| 115 | 0 | CH$_2$SCH$_2$CH$_2$OCH$_3$ | |
| 116 | 0 | CH$_2$N(CH$_3$)CH$_2$CN | |
| 117 | 0 | CH$_2$N(CH$_3$)CH(CH$_3$)$_2$ | |
| 118 | 0 | CON(CH$_3$)CH$_2$-cyclo-C$_3$H$_5$ | |
| 119 | 0 | CH$_2$N(CH$_3$)COCH$_2$OCH$_3$ | |
| 120 | 0 | CH$_2$NHCOCH$_2$CH(CH$_3$)$_2$ | |
| 121 | 0 | CON(CH$_3$)CH$_2$CN | |
| 122 | 0 | CH$_2$OCH$_2$CF$_3$ | |
| 123 | 0 | CH$_2$SC$_2$H$_5$ | |
| 124 | 0 | CH$_2$OC(O)CH$_2$CO$_2$CH$_3$ | |
| 125 | 0 | CH$_2$N(CH$_3$)SO$_2$CH$_2$CF$_3$ | oil |
| 126 | 0 | CH$_2$N(C$_2$H$_5$)CH$_2$CH=CH$_2$ | |
| 127 | 0 | CH$_2$N(CH$_3$)C(CH$_3$)$_3$ | |
| 128 | 0 | CH$_2$(O(CH$_2$)$_2$)$_2$OCH$_3$ | |
| 129 | 0 | CON(CH$_2$)$_5$ | |
| 130 | 0 | CH$_2$SCH$_2$CH$_2$OH | |
| 131 | 0 | CH$_2$NHSO$_2$CH$_2$CF$_3$ | |
| 132 | 0 | CH$_2$N(CH$_3$)CO$_2$CH$_2$CH=CH$_2$ | |
| 133 | 0 | CON(CH$_3$)CH$_2$CH$_2$OC(O)CH$_3$ | |
| 134 | 0 | CH$_2$N(CH$_3$)CO(CH$_2$)$_2$SCH$_3$ | |
| 135 | 0 | CH$_2$F | |
| 136 | 0 | CH$_2$NHCOCH$_2$SCH$_3$ | |
| 137 | 0 | CH$_2$OCO$_2$CH$_2$CH(CH$_3$)$_2$ | |
| 138 | 1 | CH$_2$SO$_2$CH$_2$CF$_3$ | |
| 139 | 0 | CH$_2$OH | crystalline |
| 140 | 0 | CH$_2$NHCH(CH$_3$)$_2$ | |
| 141 | 0 | CH$_2$OC(O)N(morpholin-4-yl) | |

TABLE 3a-continued

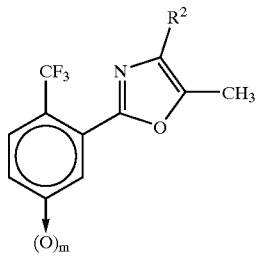

| | m | R² | Physical properties |
|---|---|---|---|
| 142 | 0 | CONHCH₂CH=CH₂ | crystalline |
| 143 | 0 | CH₂S-(1-Me-5-CF₃-imidazol-2-yl) | |
| 144 | 0 | CH₂O(CH₂)₂CH₃ | |
| 145 | 0 | CH₂NHCO-cyclo-C₄H₇ | |
| 146 | 0 | CH₂OC₂H₅ | oil |
| 147 | 0 | CH₂NHC₂H₅ | |
| 148 | 0 | CH₂N(C₂H₅)CH₂CH₂OCH=CH₂ | |
| 149 | 0 | CH₂SCH(CH₂)₅ | |
| 150 | 0 | CONHC₂H₅ | |
| 151 | 0 | CH₂OC(O)CH₂CH₂CH₃ | |
| 152 | 0 | CH₂NH-cyclo-C₃H₅ | |
| 153 | 0 | CH₂NHC(O)N(CH₃)₂ | |
| 154 | 0 | CH₂NHC(O)SCH₃ | |
| 155 | 0 | CON(CH₃)(CH₂)₂CH(CH₃)₂ | |
| 156 | 0 | CH₂N-morpholino | |
| 157 | 0 | CH₂NHCO₂CH₂CH(CH₃)₂ | |
| 158 | 0 | CH₂SO₂CH₂CF₃ | |
| 159 | 0 | CH₂NHCOCH₃ | |
| 160 | 0 | CH₂S(CH₂)₃OH | |
| 161 | 0 | CH₂CO₂C₂H₅ | oil |
| 162 | 0 | CH₂N(CH₃)CO₂C₂H₅ | |
| 163 | 0 | CONHCH₂CF₃ | |
| 164 | 0 | CH₂OCH₃ | oil |
| 165 | 0 | CH₂CO₂C(CH₃)₃ | |
| 166 | 0 | CH₂Cl | oil |
| 167 | 0 | CH₂N(CH₂)₅ | |
| 168 | 0 | CH₂NHCO-cyclo-C₃H₅ | |
| 169 | 0 | CONHC(CH₃)₃ | |
| 170 | 1 | CH₂SO₂(CH₂)₂OCH₃ | |
| 171 | 0 | CON(CH₃)CH₂CH₂CN | |
| 172 | 0 | CH₂OC(O)C(CH₃)₃ | |
| 173 | 0 | CH₂SCH₂-cyclo-C₃H₅ | |
| 174 | 0 | CH₂N(CH₃)COC₂H₅ | |
| 175 | 0 | CH₂N(C₂H₅)C(O)(CH₂)₂CH=CH₂ | |
| 176 | 0 | CONH(CH₂)₃CH₃ | oil |
| 177 | 0 | CONH(CH₂)₃OCH₃ | oil |
| 178 | 0 | CON(CH₃)CH₂CH(OCH₃)₂ | oil |
| 179 | 0 | CONHCH₂C(CH₃)₃ | m.p. 123–125° C. |
| 180 | 0 | CON(CH₃)CH₂C≡CH | wax |
| 181 | 0 | CON(CH₃)CH(CH₃)₂ | m.p. 80–81° C. |
| 182 | 0 | CONHCH₂CH(OCH₃)₂ | m.p. 75–76° C. |
| 183 | 0 | CONH-cyclohexyl | m.p. 120–121° C. |
| 184 | 0 | CON(CH₃)-cyclohexyl | m.p. 94–95° C. |

TABLE 3b

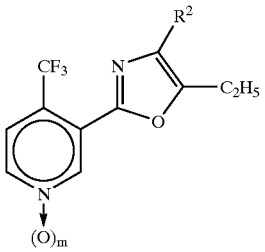

| | m | R² | Physical properties |
|---|---|---|---|
| 176a | 0 | CH₂CN | |
| 177a | 0 | CH₂S(CH₂)₂CH₃ | |
| 178a | 0 | CH₂OC(O)CO₂CH₃ | |
| 179a | 0 | CON(CH₃)(CH₂)₂CH(CH₃)₂ | |
| 180a | 0 | CH₂N(CH₃)CO₂C₂H₅ | |
| 181a | 1 | CH₂SO₂CH₃ | |
| 182a | 0 | CH₂CO₂CH₂Ph | |
| 183a | 0 | CH₂NH(CH₂)₂OCH₃ | |
| 184a | 0 | CH₂N(CH₃)C(O)N(CH₃)₂ | |
| 185 | 0 | CH₂SCH(CH₂)₄ | |
| 186 | 0 | CON(CH₃)C₂H₅ | |
| 187 | 0 | CH₂N(CH₃)COCH₂OCH₃ | |
| 188 | 0 | CH₂OCH₂CF₃ | |
| 189 | 0 | CH₂N(CH₃)SO₂CH₂CF₃ | |
| 190 | 0 | CH₂N(CH₃)CO(CH₂)₂SCH₃ | |
| 191 | 0 | CH₂NHC(O)SCH₃ | |
| 192 | 0 | CH₂SO₂CH₂CF₃ | |
| 193 | 0 | CH₂S(CH₂)₃OH | |
| 194 | 0 | CH₂SO₂(CH₂)₂OCH₃ | |
| 195 | 0 | CH₂N(CH₃)CH₂CN | |
| 196 | 0 | CH₂N(C₂H₅)CH₂CH=CH₂ | |
| 197 | 0 | CH₂N(CH₃)C(CH₃)₃ | |
| 198 | 1 | CH₂SO₂CH₂CF₃ | |
| 199 | 0 | CH₂N(CH₂)₅ | |
| 200 | 0 | CH₂N(CH₃)COCH(CH₃)₂ | |
| 201 | 0 | CH₂NHCH₂CF₃ | |
| 202 | 0 | CH₂F | |
| 203 | 0 | CONHCH₂CH=CH₂ | |
| 204 | 0 | CH₂OCH₃ | |
| 205 | 0 | CH₂NHCOCH₂SCH₃ | |
| 206 | 0 | CH₂S-(1-Me-5-CF₃-imidazol-2-yl) | |
| 207 | 0 | CH₂CO₂H | |
| 208 | 0 | CH₂OCO₂CH₃ | |
| 209 | 0 | CH₂N(CH₃)SO₂CH₃ | |
| 210 | 0 | CH₂NHCOCH=C(H)CH₃ | |
| 211 | 0 | CH₂SCH(CH₂)₅ | |
| 212 | 0 | CH₂S-(1-Me-pyrrol-2-yl) | |
| 213 | 0 | CONHC(CH₃)₃ | |
| 214 | 0 | CH₂N(C₂H₅)CH₂CH₂OCH=CH₂ | |
| 215 | 0 | CH₂OCH(CH₂)₃ | |
| 216 | 0 | CH₂N(CH₃)(CH₂)₂N(CH₃)₂ | |
| 217 | 0 | CH₂N(CH₃)CO-cyclo-C₄H₇ | |
| 218 | 0 | CH₂OCH₂CN | |
| 219 | 0 | CH₂N(CH₃)COCH₂SCH₃ | |
| 220 | 0 | CO₂-cyclo-C₃H₅ | |
| 221 | 0 | CH₂N(CH₃)-cyclo-C₆H₁₁ | |
| 222 | 0 | CH₂NHSO₂CH₂CF₃ | |
| 223 | 0 | CON(CH₃)CH₂CH₂OC(O)CH₃ | |
| 224 | 0 | CH₂OC(O)CH₂CH₂CH₃ | |

TABLE 3b-continued

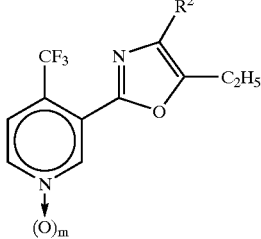

| | m | R² | Physical properties |
|---|---|---|---|
| 225 | 0 | CH₂NHC(O)N(CH₃)₂ | |
| 226 | 0 | CH₂SCH₂-cyclo-C₃H₅ | |
| 227 | 0 | CON(CH₃)₂ | |
| 228 | 0 | CON(CH₃)-n-C₃H₇ | |
| 229 | 0 | CH₂N⟨tetrahydropyridine⟩ 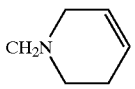 | |
| 230 | 0 | CONHCH₂CN | |
| 231 | 0 | CONH(CH₂)₂OCH₃ | |
| 232 | 0 | CH₂OC(O)CH(CH₃)₂ | |
| 233 | 0 | CH₂I | |
| 234 | 0 | CH₂N(C₂H₅)₂ | |
| 235 | 0 | CH₂CO₂CH₃ | |
| 236 | 0 | CONHCH₃ | |
| 237 | 0 | CH₂NHCO(CH₂)₂CH=CH₂ | |
| 238 | 0 | CH₂SCH₂CH(CH₃)₂ | |
| 239 | 0 | CO₂C(CH₃)₃ | |
| 240 | 0 | CH₂NHCO₂C₂H₅ | |
| 241 | 0 | CH₂OCH₂C≡CH | |
| 242 | 0 | CH₂OC(O)CH₂CH(CH₃)₂ | |
| 243 | 0 | CH₂SCH₂CH₂OH | |
| 244 | 0 | CON(CH₃)CH₂CH=CH₂ | |
| 245 | 0 | CH₂SCH₂-2-furfuryl | |
| 246 | 0 | CH₂O(CH₂)₂CH₃ | |
| 247 | 0 | CH₂CO-cyclo-C₃H₅ | |
| 248 | 0 | CON(CH₂)₅ | |
| 249 | 0 | CH₂NHCH(CH₃)₂ | |
| 250 | 0 | CH₂S(CH₂)₂N(CH₃)₂ | |
| 251 | 0 | CON(CH₃)CH(OCH₃)₂ | |
| 252 | 0 | CH₂SOCH₃ | |
| 253 | 0 | CONHCH(CH₃)₂ | |
| 254 | 0 | CH₂OC(O)CH₂CH₂Si(CH₃)₃ | |
| 255 | 0 | CH₂SCH₂-2-pyrimidyl | |
| 256 | 0 | CH₂SOCH₂-2-furfuryl | |
| 257 | 0 | CON(CH₃)-n-C₄H₉ | |
| 258 | 0 | CH₂OC(O)CH=CH₂ | |
| 259 | 0 | CON⟨N-methylpiperazine⟩  | |
| 260 | 0 | CH₂SCH₂-2-pyridyl | |
| 261 | 0 | CH₂S-⟨1,2,4-triazole⟩ 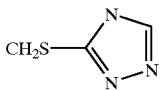 | |
| 262 | 0 | CON(CH₃)CH₂CH₂N(CH₃)₂ | |
| 263 | 0 | CH₂N(CH₃)C(O)SCH₃ | |
| 264 | 0 | CH₂SO₂CH₂-2-furfuryl | |
| 265 | 0 | CH₂OCH₂-cyclo-C₃H₅ | |
| 266 | 0 | CONH(CH₂)₃CH₃ | |
| 267 | 0 | CH₂OC₂H₅ | crystalline |
| 268 | 0 | CH₂NHC(O)SPh | |
| 269 | 0 | CH₂(O(CH₂)₂)₂OCH₃ | |
| 270 | 0 | CH₂SC(CH₃)₃ | |
| 271 | 0 | CH₂O(CH₂)₂OCH₃ | |

TABLE 3b-continued

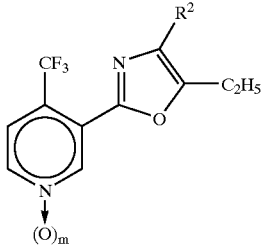

| | m | R² | Physical properties |
|---|---|---|---|
| 272 | 1 | CH₂SO₂CH₂-2-furfuryl | |
| 273 | 0 | CH₂CON(CH₃)₂ | m.p. 113–114° C. |
| 274 | 0 | CH₂OC(O)N⟨morpholine⟩ 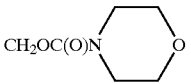 | |
| 275 | 0 | CH₂OC(O)C(CH₃)₃ | |
| 276 | 0 | CH₂Br | |
| 277 | 0 | CH₂SO₂(CH₂)₂CH₃ | |
| 278 | 0 | CONHCH₂-cyclo-C₃H₅ | |
| 279 | 0 | CH₂SOCH₂CF₃ | |
| 280 | 0 | CH₂OCH₂CH(CH₃)₂ | |
| 281 | 0 | CH₂OC(O)N(CH₃)₂ | |
| 282 | 0 | CON(CH₃)OCH₃ | |
| 283 | 0 | CH₂N(CH₃)CO₂CH₂CH(CH₃)₂ | |
| 284 | 0 | CH₂S-⟨1-methyltetrazole⟩ 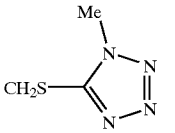 | |
| 285 | 0 | CH₂N(C₂H₅)COCH₃ | |
| 286 | 0 | CONHCH₂C≡CH | |
| 287 | 0 | CH₂N(CH₃)COCH₂-cyclo-C₅H₉ | |
| 288 | 1 | CH₂SO₂(CH₂)₂CH₃ | |
| 289 | 0 | CH₂NHCO₂CH₂CH₂Cl | |
| 290 | 0 | CH₂N(CH₃)CO-cyclo-C₃H₅ | |
| 291 | 0 | CH₂NH₂ | |
| 292 | 0 | CON⟨morpholine⟩ 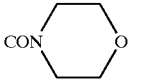 | |
| 293 | 0 | CH₂SCH₂CH₂OCH₃ | |
| 294 | 0 | CH₂N(CH₃)CH(CH₃)₂ | |
| 295 | 0 | CH₂SO₂CH₃ | |
| 296 | 0 | CON(CH₃)CH₂-cyclo-C₃H₅ | |
| 297 | 0 | CH₂NHCOCH₂CH(CH₃)₂ | |
| 298 | 0 | CH₂NHC(O)S(CH₂)₂CH₃ | |
| 299 | 0 | CON(CH₃)CH₂CN | |
| 300 | 0 | CH₂SC₂H₅ | |
| 301 | 0 | CON(CH₂)₄ | |
| 302 | 0 | CH₂OC(O)CH₂CO₂CH₃ | |
| 304 | 0 | CH₂SO(CH₂)₂OCH₃ | |
| 305 | 0 | CH₂N(CH₃)COC₂H₅ | |
| 306 | 0 | CH₂NHSO₂C₂H₅ | |
| 307 | 0 | CH₂OC(O)CH₃ | |

TABLE 3b-continued

| | m | R² | Physical properties |
|---|---|---|---|
| 308 | 0 | CO₂CH₂Ph | |
| 309 | 0 | CH₂N(CH₃)CO₂CH₂CH=CH₂ | |
| 310 | 0 | CH₂OC(O)C₂H₅ | |
| 311 | 0 | CH₂OCH₂CF₃ | |
| 312 | 0 | CH₂OCO₂CH₂CH(CH₃)₂ | |
| 313 | 0 | CH₂SO(CH₂)₂CH₃ | |
| 314 | 0 | CH₂OH | m.p. 159 . 160° C. |
| 315 | 0 | CO₂CH₃ | |
| 316 | 0 | CH₂NHC(O)N〈morpholine〉 | |
| 317 | 0 | CH₂NHCH₂C≡CH | |
| 318 | 0 | CH₂N(CH₃)CH₂CO₂CH₃ | |
| 319 | 0 | CH₂NHCO-cyclo-C₄H₇ | |
| 320 | 0 | CH₂N(CH₃)SO₂CH₂CF₃ | |
| 321 | 0 | CH₂NHC₂H₅ | |
| 322 | 0 | CH₂N(CH₃)COCH₃ | |
| 323 | 0 | CONHC₂H₅ | |
| 324 | 0 | CH₂NHCH₃ | |
| 325 | 0 | CH₂NH-cyclo-C₃H₅ | |
| 326 | 0 | CH₂N(CH₃)CO₂CH₂CH₂Cl | |
| 327 | 0 | CH₂NHSO₂CH(CH₃)₂ | |
| 328 | 0 | CH₂N〈morpholine〉 | |
| 329 | 0 | CH₂NHCO(CH₂)₂SCH₃ | |
| 330 | 0 | CH₂NHCOCH(CH₃)₂ | |
| 331 | 0 | CH₂NHCOCH₃ | |
| 332 | 0 | CH₂NHCOCH₂-cyclo-C₅H₉ | |
| 333 | 0 | CH₂SCH₂CH=CH₂ | |
| 334 | 0 | CH₂CO₂C₂H₅ | |
| 335 | 0 | CH₂NH(CH₂)₃CH₃ | |
| 336 | 0 | CONHCH₂CF₃ | |
| 337 | 0 | CH₂O(CH₂)₂CH₃ | |
| 338 | 0 | CH₂CO₂C(CH₃)₃ | |
| 339 | 0 | CH₂Cl | |
| 340 | 0 | CH₂NHCO-cyclo-C₃H₅ | |
| 341 | 0 | CONHC₃H₇ | |
| 342 | 1 | CH₂SO₂(CH₂)₂OCH₃ | |
| 343 | 0 | CON(CH₃)CH₂CH₂CN | |
| 344 | 0 | CH₂OCH₂CH=CH₂ | |
| 345 | 0 | CH₂N(C₂H₅)C(O)(CH₂)₂CH=CH₂ | |
| 346 | 0 | CH₂N(CH₃)SO₂C₂H₅ | |
| 347 | 0 | CH₂N(CH₃)COCH₃ | |
| 348 | 0 | CH₂NHCO₂CH₂CH=CH₂ | |
| 349 | 0 | CH₂SCH₃ | |
| 350 | 0 | CO₂H | |
| 351 | 0 | CH₂NHCO₂CH₂CH(CH₃)₂ | |
| 352 | 0 | CH₂N(CH₃)₂ | |

TABLE 3c

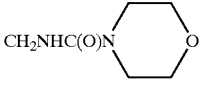

| | m | R² | Physical properties |
|---|---|---|---|
| 353 | 0 | CO₂H | m.p. 143–144° C. |
| 354 | 0 | CH₂SC₂H₅ | |
| 355 | 0 | CH₂N(CH₃)COC₂H₅ | |
| 356 | 0 | CH₂OC(O)CH₃ | |
| 357 | 0 | CH₂N(CH₃)CO₂CH₂CH=CH₂ | |
| 358 | 1 | CH₂SO₂CH₃ | |
| 359 | 0 | CON(CH₃)C₂H₅ | |
| 360 | 0 | CH₂N(CH₃)-cyclo-C₆H₁₁ | |
| 361 | 0 | CH₂OCH₂CF₃ | |
| 362 | 0 | CH₂SCH₃ | oil |
| 363 | 0 | CH₂NHSO₂CH₂CF₃ | |
| 364 | 0 | CH₂SO(CH₂)₂CH₃ | |
| 365 | 0 | CO₂CH₃ | |
| 366 | 0 | CH₂NHC(O)N〈morpholine〉 | |
| 367 | 0 | CH₂N(CH₃)CO(CH₂)₂SCH₃ | |
| 368 | 0 | CH₂S(CH₂)₃OH | |
| 369 | 1 | CH₂SO₂CH₂CF₃ | |
| 370 | 0 | CH₂N(CH₂)₅ | |
| 370a | 0 | CH₂N(CH₃)CO₂C₂H₅ | |
| 372 | 0 | CH₂CO₂CH₂Ph | |
| 373 | 0 | CH₂N(CH₃)COCH₂OCH₃ | |
| 374 | 0 | CH₂OCH₂CF₃ | |
| 375 | 0 | CH₂(O(CH₂)₂)₂OCH₃ | |
| 376 | 0 | CO₂-cyclo-C₃H₅ | |
| 377 | 0 | CONHCH₂CN | |
| 378 | 0 | CH₂SCH₂-2-pyridyl | |
| 379 | 0 | CH₂N(CH₃)CO-cyclo-C₃H₅ | |
| 380 | 0 | CH₂NHCH₂CF₃ | |
| 381 | 0 | CONHCH₂CH=CH₂ | |
| 382 | 0 | CH₂NHCOCH₂SCH₃ | |
| 383 | 0 | CH₂CO₂H | |
| 384 | 0 | CH₂N(CH₃)SO₂CH₃ | |
| 385 | 0 | CH₂OCH₂C≡CH | |
| 386 | 0 | CH₂OC(O)N(CH₃)₂ | |
| 387 | 0 | CH₂SCH(CH₃)₂ | |
| 387a | 0 | CONHC(CH₃)₃ | |
| 388 | 0 | CH₂OCH(CH₃)₂ | |
| 389 | 0 | CH₂N(CH₃)(CH₂)₂N(CH₃)₂ | |
| 390 | 0 | CH₂OC(O)CH₂CN | |
| 391 | 0 | CH₂N〈tetrahydropyridine〉 | |
| 392 | 0 | CH₂OC(O)CH(CH₃)₂ | |
| 393 | 0 | CON(CH₃)-n-C₃H₇ | |
| 394 | 0 | CON(CH₃)₂ | m.p. 62–63° C. |
| 395 | 0 | CH₂I | |
| 396 | 0 | CONHCH₃ | |
| 397 | 0 | CH₂N(CH₃)C(O)SCH₃ | |
| 398 | 0 | CH₂N(CH₃)CO₂CH₂CH(CH₃)₂ | |
| 399 | 0 | CONHC₂H₅ | |
| 400 | 0 | CH₂SCH₂CH(CH₃)₂ | |
| 401 | 0 | CO₂C(CH₃)₃ | |
| 402 | 0 | CH₂OC(O)CH₂CH(CH₃)₂ | |
| 403 | 0 | CON(CH₃)CH₂CH=CH₂ | |
| 404 | 0 | CH₂O(CH₂)₂CH₃ | |

TABLE 3c-continued

Structure: pyridine with CF$_3$ at 4-position, N-oxide (O)$_m$, connected to oxazole ring bearing R$^2$ and CH$_2$CH$_2$CH$_3$.

| # | m | R² | Physical properties |
|---|---|---|---|
| 405 | 0 | CH$_2$SO$_2$CH$_2$-2-furfuryl | |
| 406 | 0 | CON(CH$_2$)$_5$ | |
| 407 | 0 | CH$_2$SCH$_2$-2-furfuryl | |
| 408 | 0 | CON(CH$_3$)CH(OCH$_3$)$_2$ | |
| 409 | 0 | CH$_2$SOCH$_3$ | |
| 410 | 0 | CH$_2$SCH$_2$-2-pyrimidyl | |
| 411 | 0 | CH$_2$OC(O)CH=CH$_2$ | |
| 412 | 0 | CH$_2$NH-cyclo-C$_3$H$_5$ | |
| 413 | 0 | CONHCH(CH$_3$)$_2$ | |
| 414 | 0 | CH$_2$OC(O)CH$_2$CH$_2$Si(CH$_3$)$_3$ | |
| 415 | 0 | CON(piperazinyl-NCH$_3$) | |
| 416 | 0 | CH$_2$OCH$_2$-cyclo-C$_3$H$_5$ | |
| 417 | 0 | CH$_2$OC$_2$H$_5$ | |
| 418 | 0 | CH$_2$NHC(O)SPh | |
| 419 | 0 | CON(CH$_2$)$_3$ | |
| 420 | 1 | CH$_2$SO$_2$CH$_2$-2-furfuryl | |
| 421 | 0 | CH$_2$OC(O)C(CH$_3$)$_3$ | |
| 422 | 0 | CH$_2$SO$_2$(CH$_2$)$_2$CH$_3$ | |
| 423 | 0 | CH$_2$CON(CH$_3$)$_2$ | m.p. 113–114° C. |
| 424 | 0 | CH$_2$OC(O)N(morpholinyl) | |
| 425 | 0 | CONHCH$_2$-cyclo-C$_3$H$_5$ | |
| 426 | 0 | CH$_2$N(C$_2$H$_5$)COCH$_3$ | |
| 427 | 0 | CH$_2$N(CH$_3$)COCH$_2$-cyclo-C$_5$H$_9$ | |
| 428 | 0 | CH$_2$OCH$_2$CH(CH$_3$)$_2$ | |
| 429 | 0 | CH$_2$OCO$_2$CH$_3$ | |
| 430 | 0 | CON(CH$_3$)OCH$_3$ | |
| 431 | 0 | CH$_2$NHCH(CH$_3$)$_2$ | |
| 432 | 0 | CH$_2$SOCH$_2$CF$_3$ | |
| 433 | 0 | CH$_2$NHCO$_2$CH$_2$CH$_2$Cl | |
| 434 | 0 | CH$_2$N(CH$_3$)CH(CH$_3$)$_2$ | |
| 435 | 0 | CON(CH$_3$)CH$_2$-cyclo-C$_3$H$_5$ | |
| 436 | 0 | CH$_2$NHC(O)S(CH$_2$)$_2$CH$_3$ | |
| 437 | 0 | CON(CH$_3$)CH$_2$CN | |
| 439 | 0 | CH$_2$NH$_2$ | |
| 440 | 0 | CON(morpholinyl) | |
| 441 | 0 | CH$_2$NH(CH$_2$)$_2$OCH$_3$ | |
| 442 | 0 | CH$_2$N(CH$_3$)SO$_2$CH$_2$CF$_3$ | |
| 443 | 0 | CH$_2$N(C$_2$H$_5$)$_2$ | |
| 444 | 0 | CH$_2$SCH$_2$CH=CH$_2$ | |
| 445 | 0 | CON(CH$_2$)$_4$ | |
| 446 | 0 | CH$_2$SO(CH$_2$)$_2$OCH$_3$ | |
| 447 | 0 | CH$_2$NHSO$_2$C$_2$H$_5$ | |
| 448 | 0 | CO$_2$CH$_2$Ph | |
| 449 | 0 | CH$_2$NHCOCH(CH$_3$)$_2$ | |
| 450 | 0 | CH$_2$OC(O)CH$_2$CO$_2$CH$_3$ | |
| 451 | 0 | CONH(CH$_2$)$_2$OCH$_3$ | |
| 452 | 0 | CH$_2$OC(O)C$_2$H$_5$ | |
| 453 | 0 | CH$_2$OCO$_2$CH$_2$CH(CH$_3$)$_2$ | |
| 454 | 0 | CH$_2$N(CH$_3$)CH$_2$CO$_2$CH$_3$ | |
| 455 | 0 | CH$_2$NHC$_2$H$_5$ | |
| 456 | 0 | CH$_2$NHCOCH$_3$ | |
| 457 | 0 | CH$_2$OH | m.p. 70–71° C. |
| 458 | 0 | CH$_2$NHCH$_2$C≡CH | |
| 459 | 0 | CH$_2$N(CH$_3$)COCH$_3$ | |
| 460 | 0 | CH$_2$NHCH$_3$ | |
| 461 | 0 | CH$_2$N(CH$_3$)CO$_2$CH$_2$CH$_2$Cl | |
| 462 | 0 | CH$_2$N(CH$_3$)SO$_2$CH$_2$CF$_3$ | |
| 463 | 0 | CH$_2$NHSO$_2$CH(CH$_3$)$_2$ | |
| 464 | 0 | CH$_2$N(morpholinyl) | |
| 465 | 0 | CH$_2$NHCO(CH$_2$)$_2$SCH$_3$ | |
| 466 | 0 | CH$_2$NHCOCH$_2$-cyclo-C$_5$H$_9$ | |
| 467 | 0 | CH$_2$NH(CH$_2$)$_3$CH$_3$ | |
| 468 | 0 | CH$_2$O(CH$_2$)$_3$CH$_3$ | |
| 469 | 0 | CH$_2$Cl | oil |
| 470 | 0 | CH$_2$CO$_2$C$_2$H$_5$ | |
| 471 | 0 | CONHC$_3$H$_7$ | |
| 472 | 0 | CON(CH$_3$)CH$_2$CH$_2$CN | |
| 473 | 0 | CH$_2$OCH$_2$CH=CH$_2$ | |
| 474 | 0 | CH$_2$N(CH$_3$)SO$_2$C$_2$H$_5$ | |
| 475 | 0 | CH$_2$N(CH$_3$)COCH$_3$ | |
| 476 | 0 | CH$_2$CO$_2$CH$_3$ | |
| 477 | 0 | CONHCH$_2$CF$_3$ | |
| 478 | 0 | CH$_2$NHCO(CH$_2$)$_2$CH=CH$_2$ | |
| 479 | 0 | CH$_2$CO$_2$C(CH$_3$)$_3$ | |
| 480 | 0 | CH$_2$NHCOCH$_2$CH=CH$_2$ | |
| 481 | 0 | CH$_2$NHCO-cyclo-C$_4$H$_7$ | |
| 482 | 0 | CH$_2$NHCO$_2$CH$_2$CH(CH$_3$)$_2$ | |
| 483 | 0 | CH$_2$CN | |
| 484 | 0 | CON(CH$_3$)(CH$_2$)$_2$CH(CH$_3$)$_2$ | |
| 485 | 0 | CH$_2$N(CH$_3$)C(O)N(CH$_3$)$_2$ | |
| 486 | 0 | CH$_2$NHC(O)SCH$_3$ | |
| 487 | 0 | CH$_2$N(CH$_3$)COCH$_2$SCH$_3$ | |
| 488 | 0 | CH$_2$N(C$_2$H$_5$)C(O)(CH$_2$)$_2$CH=CH$_2$ | |
| 489 | 0 | CH$_2$NHCO$_2$C$_2$H$_5$ | |
| 490 | 0 | CH$_2$NHCO-cyclo-C$_3$H$_5$ | |
| 491 | 1 | CH$_2$SO$_2$(CH$_2$)$_2$OCH$_3$ | |
| 492 | 0 | CH$_2$SCH$_2$CH$_2$OH | |
| 493 | 0 | CON(CH$_3$)CH$_2$CH$_2$OC(O)CH$_3$ | |
| 494 | 0 | CH$_2$OC(O)CH$_2$CH$_2$CH$_3$ | |
| 495 | 0 | CH$_2$CO$_2$-cyclo-C$_3$H$_5$ | |
| 496 | 0 | CH$_2$S(CH$_2$)$_2$CH$_3$ | |
| 497 | 0 | CH$_2$SCH(CH$_2$)$_4$ | |
| 498 | 0 | CH$_2$SO$_2$CH$_2$CF$_3$ | |
| 499 | 0 | CH$_2$SO$_2$(CH$_2$)$_2$OCH$_3$ | |
| 500 | 0 | CH$_2$N(CH$_3$)CH$_2$CN | |
| 501 | 0 | CH$_2$N(C$_2$H$_5$)CH$_2$CH=CH$_2$ | |
| 502 | 0 | CH$_2$S-(1-Me-pyrrol-2-yl) | |
| 503 | 0 | CH$_2$N(C$_2$H$_5$)CH$_2$CH$_2$OCH=CH$_2$ | |
| 504 | 0 | CH$_2$N(CH$_3$)CO-cyclo-C$_4$H$_7$ | |

TABLE 3c-continued

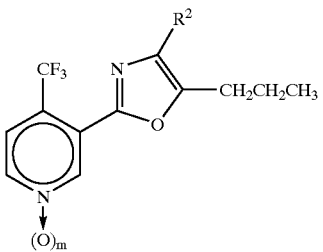

| | m | R² | Physical properties |
|---|---|---|---|
| 505 | 0 | $CH_2S(CH_2)_2N(CH_3)_2$ | |
| 506 | 0 | $CH_2SOCH_2$-2-furfuryl | |
| 507 | 0 | $CON(CH_3)$-n-$C_4H_9$ | |
| 508 | 0 | $CH_2OC(O)CO_2CH_3$ | |
| 509 | 0 | $CH_2F$ | |
| 510 | 0 | $CH_2S$—[1,2,4-triazole] | |
| 511 | 0 | $CON(CH_3)CH_2CH_2N(CH_3)_2$ | |
| 512 | 0 | $CONH(CH_2)_3CH_3$ | |
| 513 | 0 | $CH_2S$—[imidazole-N-Me, 5-$CF_3$] | |
| 514 | 0 | $CH_2NHCOCH{=}C(H)CH_3$ | |
| 515 | 0 | $CH_2SC(CH_3)_3$ | |
| 516 | 0 | $CH_2O(CH_2)_2OCH_3$ | |
| 517 | 0 | $CH_2Br$ | |
| 518 | 0 | $CH_2N(CH_3)C(CH_3)_3$ | |
| 519 | 0 | $CH_2N(CH_3)COCH(CH_3)_2$ | |
| 520 | 0 | $CH_2S$—[tetrazole-N-Me] | |
| 521 | 0 | $CONHCH_2C{\equiv}CH$ | |
| 522 | 0 | $CH_2NHC(O)N(CH_3)_2$ | |
| 523 | 1 | $CH_2SO_2(CH_2)_2CH_3$ | |
| 524 | 0 | $CH_2OCH_3$ | |
| 525 | 0 | $CH_2SCH_2CH_2OCH_3$ | |
| 526 | 0 | $CH_2SO_2CH_3$ | |
| 527 | 0 | $CH_2NHCOCH_2CH(CH_3)_2$ | |
| 528 | 0 | $CH_2SCH_2$-cyclo-$C_3H_5$ | |

TABLE 3d

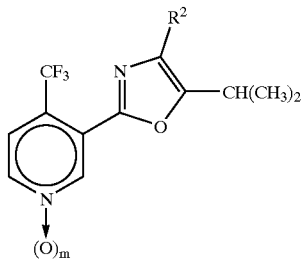

| | m | R² | Physical properties |
|---|---|---|---|
| 529 | 0 | $CONHCH_2CF_3$ | |
| 530 | 0 | $CH_2NHCH_3$ | |
| 531 | 0 | $CH_2NHC(O)$-morpholinyl | |
| 532 | 0 | $CH_2NHC(O)N(CH_3)_2$ | |
| 533 | 0 | $CH_2N(CH_3)CO_2C_2H_5$ | |
| 534 | 0 | $CH_2NHCO_2CH_2CH{=}CH_2$ | |
| 535 | 0 | $CONHC_3H_7$ | |
| 536 | 0 | $CH_2NHC(O)SCH_3$ | |
| 537 | 0 | $CH_2CO_2C(CH_3)_3$ | |
| 538 | 0 | $CH_2N(CH_3)COCH_3$ | |
| 539 | 0 | $CON(CH_3)CH_2CH_2N(CH_3)_2$ | |
| 540 | 0 | $CH_2OCH_2CF_3$ | |
| 541 | 0 | $CH_2N(CH_3)SO_2C_2H_5$ | |
| 542 | 0 | $CH_2OC(O)CH_2CN$ | |
| 543 | 0 | $CH_2CO_2CH_2Ph$ | |
| 544 | 0 | $CH_2N(C_2H_5)COCH_3$ | |
| 545 | 0 | $CON(CH_3)C_2H_5$ | |
| 546 | 0 | $CH_2OCH_2CF_3$ | |
| 547 | 0 | $CH_2NHSO_2CH_2CF_3$ | |
| 548 | 0 | $CH_2OC(O)CH_2CH_3$ | |
| 549 | 0 | $CH_2NHCOCH{=}C(H)CH_3$ | |
| 550 | 0 | $CH_2N(C_2H_5)_2$ | |
| 551 | 0 | $CON(CH_3)(CH_2)_2CH(CH_3)_2$ | |
| 552 | 0 | $CONHC(CH_3)_3$ | |
| 553 | 0 | $CO_2CH_3$ | crystalline |
| 554 | 0 | $CH_2N(CH_3)SO_2CH_2CF_3$ | |
| 555 | 0 | $CH_2N(CH_3)CO$-cyclo-$C_3H_5$ | |
| 556 | 0 | $CH_2NHSO_2CH(CH_3)_2$ | |
| 557 | 0 | $CH_2S$—[tetrazole-N-Me] | |
| 558 | 0 | $CH_2SO_2(CH_2)_2CH3$ | |
| 559 | 0 | $CH_2NHCH_2CF_3$ | |
| 560 | 0 | $CH_2SCH_2CH_2OCH_3$ | |
| 561 | 0 | $CH_2SC_2H_5$ | |
| 562 | 0 | $CH_2N(CH_3)CO_2CH_2CH{=}CH_2$ | |
| 563 | 0 | $CH_2NH(CH_2)_3CH_3$ | |
| 564 | 0 | $CH_2N(CH_3)CO_2CH_2CH_2Cl$ | |
| 565 | 0 | $CH_2OC(O)CH{=}CH_2$ | |
| 566 | 0 | $CH_2NH$-cyclo-$C_3H_5$ | |
| 567 | 0 | $CH_2NHCO_2CH_2CH(CH_3)_2$ | |
| 568 | 0 | $CH_2CO_2C_2H_5$ | |
| 569 | 0 | $CH_2Cl$ | |
| 570 | 0 | $CH_2N(CH_3)COC_2H_5$ | |
| 571 | 0 | $CH_2SO(CH_2)_2OCH_3$ | |
| 572 | 0 | $CH_2O(CH_2)_3CH_3$ | |
| 573 | 0 | $CH_2N(CH_3)CH_2CO_2CH_3$ | |
| 574 | 0 | $CH_2OC(O)CH_2CH_2Si(CH_3)_3$ | |
| 575 | 0 | $CH_2N(CH_3)COCH_3$ | |
| 576 | 0 | $CH_2N(CH_3)C(O)N(CH_3)_2$ | |
| 577 | 0 | $CH_2N(CH_3)COCH$-cyclo-$C_5H_9$ | |
| 578 | 0 | $CH_2N(CH_3)CH_2CN$ | |

TABLE 3d-continued

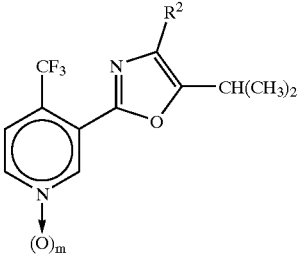

| | m | R² | Physical properties |
|---|---|---|---|
| 579 | 0 | CH₂OC(O)CH₂CO₂CH₃ | |
| 580 | 0 | CO₂C(CH₃)₃ | |
| 581 | 0 | CONHCH₃ | |
| 582 | 0 | CH₂NHCO(CH₂)₂SCH₃ | |
| 583 | 0 | 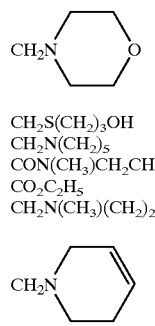 | |
| 584 | 0 | CH₂S(CH₂)₃OH | |
| 585 | 0 | CH₂N(CH₂)₅ | |
| 586 | 0 | CON(CH₃)CH₂CH₂CN | |
| 587 | 0 | CO₂C₂H₅ | |
| 588 | 0 | CH₂N(CH₃)(CH₂)₂N(CH₃)₂ | |
| 589 | 0 | 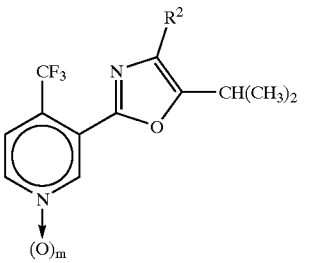 | |
| 590 | 0 | CON(CH₃)CH₂CH=CH₂ | |
| 591 | 0 | CH₂NHCOCH₂-cyclo-C₃H₉ | |
| 592 | 0 | CON(CH₂)₃ | |
| 593 | 0 | CO₂-cyclo-C₃H₅ | |
| 594 | 0 | CONHCH₂-cyclo-C₃H₅ | |
| 595 | 0 | CH₂N(CH₃)C(O)SCH₃ | |
| 596 | 0 | CH₂N(CH₃)CH(CH₃)₂ | |
| 597 | 0 | CH₂N(CH₃)SO₂CH₂CF₃ | |
| 598 | 0 | CH₂SCH₂CH(CH₃)₂ | |
| 599 | 0 | CONHCH(CH₃)₂ | |
| 600 | 0 | CH₂OCH₂CH=CH₂ | |
| 601 | 1 | CH₂SO₂(CH₂)₂OCH₃ | |
| 602 | 1 | CH₂SO₂CH₂-2-furfuryl | |
| 603 | 0 | CH₂SO(CH₂)₂CH₃ | |
| 604 | 0 | CON(CH₂)₄ | |
| 605 | 0 | CH₂OCH(CH₂)₃ | |
| 606 | 0 | CH₂OCH₂CH(CH₃)₂ | |
| 607 | 0 | CONH(CH₂)₃CH₃ | |
| 608 | 0 | CON(CH₃)CH₂-cyclo-C₃H₅ | |
| 609 | 0 | CH₂N(C₂H₅)CH₂CH=CH₂ | |
| 610 | 1 | CH₂SO₂(CH₂)₂CH₃ | |
| 611 | 0 | CONH(CH₂)₂OCH₃ | |
| 612 | 0 | CH₂S(CH₂)₂N(CH₃)₂ | |
| 613 | 0 | CH₂SO₂CH₂CF₃ | |
| 614 | 0 | CH₂NHCO-cyclo-C₃H₅ | |
| 615 | 0 | CH₂OC(O)C(CH₃)₃ | |
| 616 | 0 | CON(CH₃)₂ | m.p. 91–92° C. |
| 617 | 0 | CH₂NH(CH₂)₂OCH₃ | |
| 618 | 0 | CO₂CH₂Ph | |
| 619 | 0 | CH₂O(CH₂)₂OCH₃ | |
| 620 | 0 | CH₂SOCH₃ | |
| 621 | 0 | CH₂SCH(CH₂)₄ | |
| 622 | 0 | CH₂NHCO₂CH₂CH₂Cl | |
| 623 | 0 | CH₂N(CH₃)COCH₂OCH₃ | |
| 624 | 0 | CH₂N(CH₃)C(CH₃)₃ | |
| 625 | 0 | CH₂CO₂H | |
| 626 | 0 | CH₂SCH₂-2-furfuryl | |
| 627 | 0 | CH₂OCH₃ | |
| 628 | 0 | CH₂SO₂CH₂-2-furfuryl | |
| 629 | 0 | CH₂SCH₂CH=CH₂ | |
| 630 | 0 | CH₂Br | |
| 631 | 0 | CH₂NHC(O)SPh | |
| 632 | 0 | 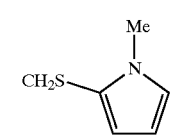 | |
| 633 | 0 | CON(CH₃)OCH₃ | |
| 634 | 0 | CH₂(O(CH₂)₂)₂OCH₃ | |
| 635 | 0 | CH₂NHCO(CH₂)₂CH=CH₂ | |
| 636 | 0 | CONHCH₂CN | |
| 637 | 0 | CH₂NHCH₂C≡CH | |
| 638 | 0 | CH₂I | |
| 639 | 0 | CH₂OC(O)CH(CH₃)₂ | |
| 640 | 0 | CH₂NHCO₂C₂H₅ | |
| 641 | 0 | CH₂S(CH₂)₂CH₃ | |
| 642 | 0 | CH₂N(CH₃)COCH(CH₃)₂ | |
| 643 | 0 | CON(CH₂)₅ | |
| 644 | 0 | 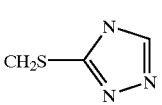 | |
| 645 | 0 | CONHCH₂C≡CH | |
| 646 | 0 | CH₂CON(CH₃)₂ | |
| 647 | 0 | CH₂SOCH₂CF₃ | |
| 648 | 0 | CH₂N(CH₃)CO₂CH₂CH(CH₃)₂ | |
| 649 | 0 | CH₂NH₂ | |
| 650 | 0 | CH₂SC(CH₃)₃ | |
| 651 | 0 | CH₂SCH₂-2-pyridyl | |
| 652 | 0 | CH₂OCH₂C≡CH | |
| 653 | 0 | CH₂OC(O)CH₂CH(CH₃)₂ | |
| 654 | 0 | CH₂SCH₂CH₂OH | |
| 655 | 0 | CH₂SOCH₂-2-furfuryl | |
| 656 | 0 | CH₂OH | crystalline |
| 657 | 0 | CH₂CO₂CH₃ | |
| 658 | 0 |  | |
| 659 | 0 | CON(CH₃)CH₂CN | |
| 660 | 0 | CH₂SCH₂-2-pyrimidyl | |
| 661 | 0 | CH₂OCH₂-cyclo-C₃H₅ | |
| 662 | 0 | CON(CH₃)-n-C₃H₇ | |
| 663 | 0 | CH₂OC(O)CH₃ | |
| 664 | 0 | CH₂NHSO₂C₂H₅ | |
| 665 | 0 | CON(CH₃)-n-C₄H₉ | |
| 666 | 0 | CH₂N(CH₃)-cyclo-C₆H₁₁ | |
| 667 | 0 | CH₂OC(O)C₂H₅ | |

TABLE 3d-continued

[Structure: pyridine with CF3, N-oxide (O)m, linked to oxazole bearing R² and CH(CH3)2]

| | m | R² | Physical properties |
|---|---|---|---|
| 668 | 0 | CON(CH₃)CH(OCH₃)₂ | |
| 669 | 0 | CH₂NHC(O)S(CH₂)₂CH₃ | |
| 670 | 0 | CH₂SO₂CH₃ | |
| 671 | 0 | CH₂NHCH(CH₃)₂ | |
| 672 | 0 | CH₂NHCOCH(CH₃)₂ | |
| 673 | 0 | CH₂N(CH₃)COCH₂SCH₃ | |
| 674 | 0 | CH₂CO₂-cyclo-C₃H₅ | |
| 675 | 0 | CH₂N(CH₃)CO-cyclo-C₄H₇ | |
| 676 | 0 | CH₂OC(O)N(CH₃)₂ | |
| 677 | 0 | CON-morpholinyl | |
| 678 | 0 | CH₂OC(O)N-morpholinyl | |
| 679 | 0 | CH₂NHCOCH₃ | |
| 680 | 0 | CON(CH₃)CH₂CH₂OC(O)CH₃ | |
| 681 | 0 | CH₂N(CH₃)SO₂CH₃ | |
| 682 | 0 | CH₂NHC₂H₅ | |
| 683 | 0 | CONHCH₂CH═CH₂ | |
| 684 | 0 | CH₂SO₂(CH₂)₂OCH₃ | |
| 685 | 0 | CH₂N(C₂H₅)CH₂CH₂OCH═CH₂ | |
| 686 | 0 | CH₂F | |
| 687 | 0 | CH₂SCH(CH₂)₅ | |
| 688 | 0 | CH₂NHCOCH₂SCH₃ | |
| 689 | 0 | CH₂O(CH₂)₂CH₃ | |
| 690 | 0 | CH₂OCO₂CH₂CH(CH₃)₂ | |
| 691 | 0 | CH₂NHCO-cyclo-C₄H₇ | |
| 692 | 0 | CH₂OCO₂CH₃ | |
| 693 | 0 | CH₂NHCOCH₂CH(CH₃)₂ | |
| 694 | 1 | CH₂SO₂CH₂CF₃ | |
| 695 | 1 | CH₂SO₂CH₃ | |
| 697 | 0 | CH₂OC₂H₅ | |
| 698 | 0 | CH₂SCH₂-cyclo-C₃H₅ | |
| 699 | 0 | CH₂N(C₂H₅)C(O)(CH₂)₂CH═CH₂ | |
| 700 | 0 | CH₂N(CH₃)CO(CH₂)₂SCH₃ | |
| 701 | 0 | CH₂S-(1-methyl-5-CF₃-imidazol-2-yl) | |
| 702 | 0 | CH₂OC(O)CO₂CH₃ | |
| 703 | 0 | CH₂CN | |
| 704 | 0 | CONHC₂H₅ | |

TABLE 3e

[Structure: pyridine with CF3, N-oxide (O)m, linked to oxazole bearing R₂ and cyclopropyl]

| | m | R² | Physical properties |
|---|---|---|---|
| 705 | 0 | CONHCH₂CF₃ | |
| 706 | 0 | CH₂N(CH₃)COCH₃ | oil |
| 707 | 0 | CH₂NHSO₂CH₂CF₃ | |
| 708 | 0 | CH₂NHSO₂CH(CH₃)₂ | |
| 709 | 0 | CH₂OC(O)CH═CH₂ | |
| 710 | 0 | CO₂C(CH₃)₃ | |
| 711 | 0 | CON(CH₂)₃ | |
| 712 | 0 | CH₂OCH(CH₂)₃ | |
| 713 | 0 | CH₂NH(CH₂)₂OCH₃ | |
| 714 | 0 | CH₂NHC(O)SPh | |
| 715 | 0 | CH₂OC(O)CH(CH₃)₂ | |
| 716 | 0 | CH₂OC(O)CH₂CH(CH₃)₂ | |
| 717 | 0 | CH₂NHCOCH₂SCH₃ | |
| 718 | 0 | CH₂OCH(CH₃)₂ | oil |
| 719 | 0 | CH₂NHCH₃ | oil |
| 720 | 0 | CON(CH₃)CH₂CH₂N(CH₃)₂ | |
| 721 | 0 | CH₂OC(O)CH₂CH₂CH₃ | |
| 722 | 0 | CH₂S-(1-Me-tetrazol-5-yl) | |
| 723 | 0 | CH₂NH-cyclo-C₃H₅ | |
| 724 | 0 | CH₂OC(O)CH₂CO₂C₂H₅ | |
| 725 | 0 | CONHCH₃ | |
| 726 | 0 | CH₂NHCOCH₂-cyclo-C₅H₉ | |
| 727 | 0 | CON(CH₂)₄ | |
| 728 | 0 | CON(CH₃)₂ | m.p. 105–106° C. |
| 729 | 0 | CON-(4-methylpiperazinyl) | |
| 730 | 0 | CH₂S(CH₂)₃CH₃ | |
| 731 | 0 | CH₂SCH₂-2-pyridyl | |
| 732 | 0 | CON(CH₃)CH(OCH₃)₂ | |
| 733 | 0 | CON(CH₃)CH₂CH₂OC(O)CH₃ | |
| 734 | 0 | CH₂O(CH₂)₂CH₃ | |
| 735 | 0 | CH₂NHCO-cyclo-C₄H₇ | |
| 736 | 0 | CH₂N(C₂H₅)C(O)(CH₂)₂CH═CH₂ | |
| 737 | 0 | CH₂NHC(O)N-morpholinyl | |
| 738 | 0 | CH₂OCH₂CF₃ | |
| 739 | 0 | CH₂NHCOCH═C(H)CH₃ | |
| 740 | 0 | CH₂SO₂(CH₂)₂CH3 | |
| 741 | 0 | CH₂NHCO₂CH₂CH(CH₃)₂ | |
| 742 | 0 | CH₂NHCO(CH₂)₂SCH₃ | |
| 743 | 0 | CON(CH₃)CH₂CH═CH₂ | |
| 744 | 0 | CH₂SCH₂CF₃ | oil |
| 745 | 0 | CH₂OC(O)C(CH₃)₃ | |
| 746 | 0 | CON(CH₃)OCH₃ | |
| 747 | 0 | CONHCH₂C≡CH | |
| 748 | 0 | CH₂OH | crystalline |
| 749 | 0 | CH₂OC(O)C₂H₅ | |

TABLE 3e-continued

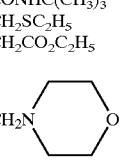

| | m | R² | Physical properties |
|---|---|---|---|
| 750 | 0 | CH₂N(CH₃)SO₂CH₃ | |
| 751 | 0 | CH₂OCO₂CH₂CH(CH₃)₂ | |
| 752 | 0 | CH₂N(CH₃)CO(CH₂)₂SCH₃ | |
| 753 | 0 | CH₂NHC(O)N(CH₃)₂ | |
| 754 | 0 | CH₂N(CH₃)SO₂C₂H₅ | |
| 755 | 0 | CH₂N(C₂H₅)₂ | |
| 756 | 0 | CH₂NHCH₂CF₃ | |
| 757 | 0 | CH₂N(CH₃)COC₂H₅ | |
| 758 | 0 | CH₂N(CH₃)C(O)N(CH₃)₂ | |
| 759 | 0 | CH₂N(CH₂)₅ | |
| 760 | 0 | CO₂-cyclo-C₃H₅ | |
| 761 | 1 | CH₂SO₂(CH₂)₂CH₃ | |
| 762 | 0 | CH₂OCH₂CH(CH₃)₂ | |
| 763 | 0 | CH₂S(CH₂)₂N(CH₃)₂ | |
| 764 | 0 | CO₂CH₂Ph | |
| 765 | 0 | CH₂N(CH₃)C(CH₃)₃ | |
| 766 | 0 | CH₂Br | |
| 767 | 0 | CH₂NHCO₂C₂H₅ | |
| 768 | 0 | CH₂SC(CH₃)₃ | |
| 769 | 0 | CH₂OCH₂-cyclo-C₃H₅ | |
| 770 | 0 | CH₂CO₂-cyclo-C₃H₅ | |
| 771 | 0 | CH₂F | |
| 772 | 0 | CH₂OCO₂CH₃ | |
| 773 | 0 | CH₂OC₂H₅ | oil |
| 774 | 0 | CH₂OC(O)CO₂CH₃ | |
| 775 | 0 | CH₂N(CH₃)CO₂C₂H₅ | |
| 776 | 0 | CH₂OC(O)CH₂CN | |
| 777 | 0 | CON(CH₃)(CH₂)₂CH(CH₃)₂ | |
| 778 | 0 | CH₂SCH₂CH₂OCH₃ | |
| 779 | 0 | CH₂Cl | oil |
| 780 | 0 | CH₂N(CH₃)COCH₂-cyclo-C₅H₉ | |
| 781 | 0 | CH₂S(CH₂)₃OH | |
| 782 | 0 | CH₂N(CH₃)C(O)SCH₃ | |
| 783 | 1 | CH₂SO₂CH₂-2-furfuryl | |
| 784 | 0 | CONH(CH₂)₃CH₃ | |
| 785 | 0 | CH₂SO₂CH₂CF₃ | |
| 786 | 0 | CH₂O(CH₂)₂OCH₃ | |
| 787 | 0 | CH₂CO₂H | |
| 788 | 0 | CH₂NHCO(CH₂)₂CH=CH₂ | |
| 789 | 0 | CH₂OCH₂C≡CH | |
| 790 | 0 | CH₂SCH₂CH₂OH | |
| 791 | 0 | CON(CH₃)-n-C₃H₇ | |
| 792 | 0 | CH₂NHC(O)S(CH₂)₂CH₃ | |
| 793 | 0 | CH₂N(CH₃)COCH₂SCH₃ | |
| 794 | 0 | CH₂OC(O)N(morpholine) | |
| 795 | 0 | CH₂SCH(CH₂)₅ | |
| 796 | 0 | CH₂NHCOCH₂CH(CH₃)₂ | |
| 797 | 0 | CH₂SCH₂-cyclo-C₃H₅ | |
| 798 | 0 | CH₂S-(1-methyl-5-CF₃-imidazol-2-yl) | |
| 799 | 0 | CH₂SCH₂CH₂CH₃ | oil |
| 800 | 0 | CH₂NHCO₂CH₂CH=CH₂ | |
| 801 | 0 | CH₂CO₂CH₂Ph | |
| 802 | 0 | CONHC(CH₃)₃ | |
| 803 | 0 | CH₂SC₂H₅ | |
| 804 | 0 | CH₂CO₂C₂H₅ | |
| 805 | 0 | CH₂N(morpholine) | |
| 806 | 0 | CH₂N(1,2,3,6-tetrahydropyridine) | |
| 807 | 0 | CH₂N(CH₃)CH(CH₃)₂ | |
| 808 | 0 | CH₂SO(CH₂)₂CH₃ | |
| 809 | 0 | CON(CH₃)CH₂-cyclo-C₃H₅ | |
| 810 | 0 | CH₂NHCO-cyclo-C₃H₅ | |
| 811 | 0 | CH₂SOCH₃ | |
| 812 | 0 | CH₂SCH₂-2-furfuryl | |
| 813 | 0 | CH₂(O(CH₂)₂)₂OCH₃ | |
| 814 | 0 | CH₂I | |
| 815 | 0 | CH₂CON(CH₃)₂ | |
| 816 | 0 | CH₂CO₂CH₃ | |
| 817 | 0 | CH₂OC(O)CH₃ | |
| 818 | 0 | CH₂SO₂CH₃ | |
| 819 | 0 | CON(morpholine) | |
| 820 | 0 | CH₂NHC₂H₅ | |
| 821 | 0 | CH₂CN | |
| 822 | 0 | CONHC₃H₇ | |
| 823 | 0 | CH₂N(C₂H₅)COCH₃ | |
| 824 | 0 | CO₂CH₃ | crystalline |
| 825 | 0 | CH₂N(CH₃)CO₂CH₂CH=CH₂ | |
| 826 | 0 | CH₂SO(CH₂)₂OCH₃ | |
| 827 | 0 | CH₂N(CH₃)COCH₃ | |
| 828 | 0 | CON(CH₃)CH₂CH₂CN | |
| 829 | 0 | CONHCH₂-cyclo-C₃H₅ | |
| 830 | 0 | CH₂OCH₂CH=CH₂ | |
| 831 | 0 | CONH(CH₂)₂OCH₃ | |
| 832 | 0 | CH₂N(CH₃)COCH₂OCH₃ | |
| 833 | 0 | CH₂SCH₂CH=CH₂ | |
| 834 | 0 | CH₂N(CH₃)COCH(CH₃)₂ | |
| 835 | 0 | CH₂NH₂ | |
| 836 | 0 | CH₂SCH₂-2-pyrimidyl | |
| 837 | 0 | CH₂N(CH₃)-cyclo-C₆H₁₁ | |
| 838 | 0 | CH₂NHCOCH(CH₃)₂ | |
| 839 | 0 | CH₂N(CH₃)CO-cyclo-C₄H₇ | |
| 840 | 0 | CH₂N(C₂H₅)CH₂CH₂OCH=CH₂ | |
| 841 | 0 | CO₂H | m.p. 188–189° C. |
| 842 | 0 | CH₂NHC(O)SCH₃ | |
| 843 | 0 | CON(CH₃)C₂H₅ | |
| 844 | 0 | CH₂N(CH₃)SO₂CH₂CF₃ | |
| 845 | 0 | CH₂NH(CH₂)₃CH₃ | |
| 846 | 0 | CH₂O(CH₂)₃CH₃ | |
| 847 | 0 | CH₂OC(O)CH₂CH₂Si(CH₃)₃ | |

TABLE 3e-continued

[Structure: pyridine with CF3 substituent connected to an oxazole ring bearing R2 and cyclopropyl; pyridine N has (O)m]

| | m | R² | Physical properties |
|---|---|---|---|
| 848 | 0 | CO₂C₂H₅ | crystalline |
| 849 | 0 | CONHCH(CH₃)₂ | |
| 850 | 1 | CH₂SO₂(CH₂)₂CH₃ | |
| 851 | 0 | CH₂NHCO₂CH₂CH₂Cl | |
| 852 | 0 | CH₂SO₂CH₂-2-furfuryl | |
| 853 | 0 | CONHCH₂CN | |
| 854 | 0 | CON(CH₂)₅ | |
| 855 | 0 | CH₂N(CH₃)CO₂CH₂CH(CH₃)₂ | |
| 856 | 0 | CON(CH₃)CH₂CN | |
| 857 | 0 | CON(CH₃)-n-C₄H₉ | |
| 858 | 0 | CH₂SO₂(CH₂)₂OCH₃ | |
| 859 | 1 | CH₂SO₂CH₃ | |
| 860 | 0 | CH₂SCH₂CH(CH₃)₂ | oil |
| 861 | 0 | CH₂CO₂C(CH₃)₃ | |
| 862 | 0 | CH₂OCH₂CF₃ | |
| 863 | 0 | CH₂N(CH₃)CO-cyclo-C₃H₅ | oil |
| 864 | 0 | CH₂N(CH₃)CO₂CH₂CH₂Cl | |
| 865 | 0 | CH₂N(CH₃)CH₂CO₂CH₃ | |
| 866 | 0 | CH₂N(CH₃)(CH₂)₂N(CH₃)₂ | |
| 867 | 0 | CH₂N(CH₃)SO₂CH₂CF₃ | crystalline |
| 868 | 0 | CH₂N(C₂H₅)CH₂CH=CH₂ | |
| 869 | 0 | CH₂SCH(CH₂)₄ | |
| 870 | 0 | CH₂OCH₃ | oil |
| 871 | 0 | CH₂NHCH₂C≡CH | |
| 872 | 0 | CH₂S-(N-methylpyrrole) | |
| 873 | 0 | CH₂SOCH₂CF₃ | |
| 874 | 0 | CH₂S-(1,2,4-triazole) | |
| 875 | 0 | CH₂NHSO₂C₂H₅ | |
| 876 | 0 | CH₂NHCH(CH₃)₂ | |
| 877 | 0 | CH₂OC(O)N(CH₃)₂ | |
| 878 | 0 | CONHCH₂CH=CH₂ | |
| 879 | 1 | CH₂SO₂CH₂CF₃ | |
| 880 | 0 | CH₂SCH₃ | oil |
| 881 | 0 | CONHC₂H₅ | |
| 882 | 0 | CH₂SOCH₂-2-furfuryl | |
| 883 | 0 | CH₂N(CH₃)CH₂CN | |
| 884 | 0 | CH₂NHCOCH₃ | |

B. FORMULATION EXAMPLES a) A dusting powder is obtained by mixing 10 parts by weight of active compound and 90 parts by weight of talc, as inert substance, and comminuting the mixture in an impact mill.

b) A wettable powder which is readily dispersible in water is obtained by mixing 25 parts by weight of active compound, 65 parts by weight of kaolin-containing quartz, as the inert substance, 10 parts by weight of potassium ligninsulfonate and 1 part by weight of sodium oleoylmethyltaurinate, as wetting and dispersing agent, and grinding the mixture in a pinned disk mill.

c) A dispersion concentrate which is readily dispersible in water is prepared by mixing 40 parts by weight of active compound with 7 parts by weight of a sulfosuccinic monoester, 2 parts by weight of a sodium ligninsulfonate and 51 parts by weight of water and grinding the mixture to a fineness of below 5 microns in a grinding bead mill.

d) An emulsifiable concentrate can be prepared from 15 parts by weight of active compound, 75 parts by weight of cyclohexane, as the solvent, and 10 parts by weight of ethoxylated nonylphenol (10 EO), as the emulsifier.

e) Granules can be prepared from 2 to 15 parts by weight of active compound and an inert granule carrier material, such as attapulgite, pumice granules and/or quartz sand. A suspension of the wettable powder from Example b) having a solids content of 30% is expediently used, and this is sprayed onto the surface of attapulgite granules and the components are dried and mixed intimately. The weight content of the wettable powder is approximately 5% and that of the inert carrier material is approximately 95% of the finished granules.

C. BIOLOGICAL EXAMPLES

Example 1

Germinated broad bean seeds (*Vicia faba*) with radicles were transferred into brown glass bottles filled with tap water and subsequently populated with approximately 100 black bean aphids (*Aphis fabae*). Plants and aphids were then dipped for 5 seconds into an aqueous solution of the formulated preparation to be examined. After the solution had dripped off, plants and animals were kept in a climatized chamber (16 hours of light/day, 25° C., 40–60% relative atmospheric humidity). After 3 and 6 days storage, the effect of the preparation on the aphids was determined. At a concentration of 300 ppm (based on the content of active compound), the preparations of Example Nos. 1/37, 1/78, 1/136, 1/94, 1/174, 1/14, 1/125, 1/187, 1/17, 1/84, 1/52, 1/82, 1/70, 3/74, 1/54, 1/81, 1/42, 3/161, 1/186 effected a mortality of 90–100% among the aphids. (The active compounds are numbered with the Table/No. in the table).

Example 2

The leaves of 12 rice plants having a stem length of 8 cm were dipped for 5 seconds into an aqueous solution of the formulated preparation to be examined. After the solution had dripped off, the rice plants treated in this manner were placed in a Petri dish and populated with approximately 20 larvae (L3 stage) of the rice leafhopper species *Nilaparvata lugens*. The Petri dish was closed and stored in a climatized chamber (16 hours of light/day, 25° C., 40–60% relative atmospheric humidity). After 6 days storage, the mortality among the leafhopper larvae was determined. At a concentration of 300 ppm (based on the content of active compound), the preparations of Example Nos. 1/53, 1/26, 1/164, 1/174, 1/82, 1/42 effected a mortality of 90–100%.

Example 3

Germinated broad bean seeds (*Vicia faba*) with radicles were transferred into brown glass bottles filled with tap water. Four milliliters of an aqueous solution of the formulated preparation to be examined were pipetted into the brown glass bottle. The broad bean was subsequently heavily populated with approximately 100 black bean aphids (*Aphis fabae*). Plants and animals were then stored in a climatized chamber (16 hours of light/day, 25° C., 40–60% relative atmospheric humidity). After 3 and 6 days storage, the root-systemic activity of the preparation on the aphids was determined. At a concentration of 30 ppm (based on the content of active compound), the preparations of Example Nos. 1/53, 1/26, 1/37, 1/78, 1/136, 1/56, 1/94, 1/174, 1/14, 1/187, 1/84, 1/52, 1/82, 1/70, 1/32, 3/74, 1/54, 1/81, 1/42, 3/227, 3/161 effected a mortality of 90–100% among the aphids by root-systemic action.

What is claimed is:

1. A 4-trifluoromethyl-3-oxazolyl compound of the formula (I)

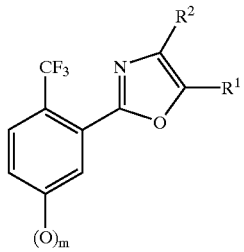

wherein:
m is 0 or 1;
$R^1$ and $R^2$ are
a) H, $CH_3$, $-C_2H_5$, $-CH_2-CH_2-CH_3-$, $CH_2(CH_3)_2$ or cyclopropyl or
b) $-CH_3$, $CH_2XR^3$, $-CHY$, $-CO_2R^4$ or $-CONR^5R^6$,
where in each case one of the radicals $R^1$, $R^2$ is one of the group a and the other is of the group b;
X is O, S, SO, $SO_2$ or $NR^7$;
Y is O, $BR_2$, $((C_1-C_4)\text{-alkoxy})_2$, $((C_1-C_4)\text{-alkylthio})_2$, $V-(CH_2)_2$ or $3-V$, where V=O, S, where an H atom is replaced or not replaced by $(C_1-C_4)$ alkyl;
$R^3$ is $R^8$, $COR^9$, $CO_2R^{10}$, $CONR^{11}R^{12}$ or, if X is O or $NR^7$, is $SO_2R^{13}$;
$R^4$, $R^5$, $R^6$, $R^7$, $R^8$, $R^9$, $R^{10}$, $R^{11}$, $R^{12}$, $R^{13}$ are identical or different and are independently of one another H, $(C_1-C_{10})$-alkyl, $(C_2-C_{10})$-alkenyl, $(C_2-C_{10})$-alkynyl, $(C_3-C_8)$-cycloalkyl, $(C_4-C_8)$-cycloalkenyl, $(C_6-C_8)$-cycloalkynyl aryl or heterocyclyl, where each of the eight last-mentioned groups is unsubstituted or mono-or polysubstituted, and where in each case $R^5$ and $R^6$ and $R^{11}$ and $R^{12}$ together are $-(CH_2)_4-$, $-(CH_2)_5-$, $-(CH_2)_2-O-(CH_2)_2-$ or $-(CH_2)_2-NR^4-(CH_2)_2-$;
with the proviso, that the compounds in which $R^1=CO_2C_2H_5$ and $R^2=H$,
$R^1=H$ and $R^2=CH_2NHC_6H_5$,
$R^1=CH_3$ and $R^2=CO_2H$,
$R^1=CH_3$ and $R^2=CO_2C_2H_5$
$R^1=CH_3$ and $R^2=CON(CH_3)_2$
$R^1=CH(CH_3)_2$ and $R^2=CO_2H$,
$R^1=CH(CH_3)_2$ and $R^2$ $CO_2C_2H_5$ are not included.

2. A 4-trifluoromethyl-3-oxazolylpyridine as claimed in claim 1, wherein $R^1$ is H and $R^2$ is a radical of the group b.

3. A 4-trifluoromethyl-3-oxazolylpyridine as claimed in claim 1, wherein $R^1$ is a radical of the group b and $R^2$ is H.

4. A 4-trifluoromethyl-3-oxazolylpyridine as claimed in claim 1, wherein $R^1$ is a radical of the group a, with the exception of hydrogen, and $R^2$ is a radical of the group b.

5. A process for preparing compounds of the formula (I) as claimed in claim 1, which comprises reacting compounds of formula (II) where $R^1$ and $R^2$ are as defined in the formula (I) in claim 1 with a dehydrating agent,

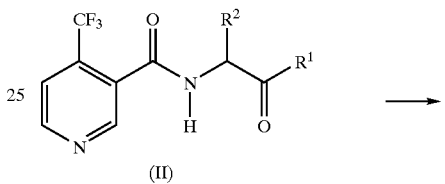

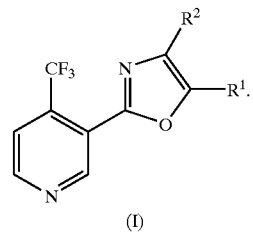

6. A composition having insecticidal, acaricidal or nematicidal action, comprising a mixture of at least one compound of the formula (I) as claimed in claim 1 with a carrier substance and optionally with a surface-active substance.

7. A method for controlling harmful insects, acarids and nematodes, which comprises applying an effective amount of a compound as claimed in claim 1 to the site of the desired action.

8. A method for controlling harmful insects, acarids and nematodes, which comprises applying an effective amount of a composition as claimed in claim 6 to the site of the desired action.

9. The process according to claim 5, wherein the dehydrating agent is selected from the group consisting of inorganic acid chlorides, inorganic acids and anhydrides.

* * * * *